US010046002B2

(12) United States Patent
Zebala et al.

(10) Patent No.: US 10,046,002 B2
(45) Date of Patent: Aug. 14, 2018

(54) METHOD FOR TREATING CANCER USING CHEMOKINE ANTAGONISTS

(71) Applicant: SYNTRIX BIOSYSTEMS INC., Auburn, WA (US)

(72) Inventors: John A. Zebala, Issaquah, WA (US); Dean Y. Maeda, Seattle, WA (US); Aaron D. Schuler, Auburn, WA (US)

(73) Assignee: SYNTRIX BIOSYSTEMS INC., Auburn, WA (US)

( * ) Notice: Subject to any disclaimer, the term of this patent is extended or adjusted under 35 U.S.C. 154(b) by 0 days.

(21) Appl. No.: 15/354,936

(22) Filed: Nov. 17, 2016

(65) Prior Publication Data

US 2017/0128474 A1 May 11, 2017

(51) Int. Cl.

| A61K 31/69 | (2006.01) |
| A61K 31/282 | (2006.01) |
| A61K 9/00 | (2006.01) |
| A61K 45/06 | (2006.01) |
| A61K 31/495 | (2006.01) |
| C07K 16/28 | (2006.01) |
| A61K 39/395 | (2006.01) |
| A61K 35/17 | (2015.01) |
| A61K 39/00 | (2006.01) |
| G01N 33/574 | (2006.01) |
| A61K 9/10 | (2006.01) |
| A61K 47/38 | (2006.01) |
| A61K 9/16 | (2006.01) |
| A61K 35/12 | (2015.01) |

(52) U.S. Cl.
CPC ............ *A61K 31/69* (2013.01); *A61K 9/0053* (2013.01); *A61K 9/0095* (2013.01); *A61K 9/10* (2013.01); *A61K 9/1652* (2013.01); *A61K 31/282* (2013.01); *A61K 31/495* (2013.01); *A61K 35/17* (2013.01); *A61K 39/0011* (2013.01); *A61K 39/3955* (2013.01); *A61K 45/06* (2013.01); *A61K 47/38* (2013.01); *C07K 16/2818* (2013.01); *G01N 33/574* (2013.01); *G01N 33/57492* (2013.01); *A61K 2035/124* (2013.01); *A61K 2039/505* (2013.01); *G01N 2333/521* (2013.01)

(58) Field of Classification Search
CPC ................................ C07F 5/025; A61K 31/69
See application file for complete search history.

(56) References Cited

U.S. PATENT DOCUMENTS

| 4,139,623 A | 2/1979 | Jaeggi et al. |
| 5,296,506 A | 3/1994 | Kingston et al. |
| 5,405,972 A | 4/1995 | Holton et al. |
| 5,411,984 A | 5/1995 | Kingston et al. |
| 5,422,364 A | 6/1995 | Nicolaou et al. |
| 5,440,057 A | 8/1995 | Nicolaou et al. |
| 5,461,169 A | 10/1995 | Nicolaou et al. |
| 5,468,769 A | 11/1995 | Klein et al. |
| 5,475,120 A | 12/1995 | Rao |
| 5,478,736 A | 12/1995 | Nair |
| 5,478,854 A | 12/1995 | Farina et al. |
| 5,480,884 A | 1/1996 | Thal et al. |
| 5,484,809 A | 1/1996 | Hostetler et al. |
| 5,488,116 A | 1/1996 | Danishefsky et al. |
| 5,489,589 A | 2/1996 | Wittman et al. |
| 5,508,447 A | 4/1996 | Magnus |
| 5,527,924 A | 6/1996 | Danishefsky et al. |
| 5,530,020 A | 6/1996 | Gunawardana et al. |
| 5,565,478 A | 10/1996 | Kohn et al. |
| 5,569,729 A | 10/1996 | Leclerc |
| 5,756,524 A | 5/1998 | Riordan et al. |
| 6,022,884 A | 2/2000 | Mantlo et al. |
| 6,093,723 A | 7/2000 | Miao et al. |
| 6,521,395 B1 | 2/2003 | Begley et al. |
| 6,777,432 B1 | 8/2004 | Cutshall et al. |
| 6,812,226 B2 | 11/2004 | Baxter et al. |
| 7,084,164 B2 | 8/2006 | Tobe et al. |
| 7,176,310 B1 | 2/2007 | Baughman et al. |
| 7,482,355 B2 | 1/2009 | Ebden et al. |
| 7,494,987 B2 | 2/2009 | Akada et al. |
| 7,759,373 B2 | 7/2010 | Hongu et al. |
| 8,637,529 B2 | 1/2014 | Woller et al. |
| 8,748,623 B2 * | 6/2014 | Maeda ................... A61K 31/44 546/268.4 |
| 8,779,149 B2 * | 7/2014 | Maeda ................... A61K 31/44 546/268.4 |
| 8,969,365 B2 * | 3/2015 | Maeda ......................... 514/274 |

(Continued)

FOREIGN PATENT DOCUMENTS

| CN | 1402730 A | 3/2003 |
| JP | H06-505027 A | 6/1994 |

(Continued)

OTHER PUBLICATIONS

P. Saintigny et al., 73 Cancer Research, 571-582 (2013).*
S.L. Highfill et al., 6 Science translational medicine, 1-15 (2014).*
S. Acharyya et al., 150 Cell, 165-178 (2012).*
S. Singh et al., 15 Clinical Cancer Research, 2380-2386 (2009).*
C. Murphy et al., 11 Clinical Cancer Research, 4117-4127 (2005).*
J. Dwyer et al., 7 PLOS one, 4117-4127 (2012).*
K.M. Hertzer et al., 17 Expert opinion on therapeutic targets, 667-680 (2013).*
U.S. Appl. No. 14/226,672, filed Mar. 26, 2014, Maeda et al.
U.S. Appl. No. 14/283,118, filed May 20, 2014, Maeda et al.
Arenberg et al., "Epithelial-Neutrophil Activating Peptide (ENA-78) Is an Important Angiogenic Factor in Non-Small Cell Lung Cancer", J. Clin. Invest., 1998, 102, 465-472.
Arenberg et al., "Inhibition of Interleukin-8 Reduces Tumorigenesis of Human Non-Small Cell Lung Cancer in SCID Mice", J. Clin. Invest., 1996, 97, 2792-2802.
Baggiolini et al., "Interleukin-8, A Chemotactic and Inflammatory Cytokine", Fed. of European Biochemical Societies, 1992, 307(1), 97-101.

(Continued)

*Primary Examiner* — Alexander R Pagano
(74) *Attorney, Agent, or Firm* — Baker & Hostetler LLP; Peter J. Knudsen

(57) ABSTRACT

What is described is a method for treating cancer in a patient in need of such treatment through the use of an antagonist to CXCR1 and/or CXCR2 receptors by administering a therapeutically effective amount of an antagonist of CXCR1 and/or CXCR2, or pharmaceutical compositions thereof, either alone as monotherapy, or in combination with at least one other anticancer therapy.

22 Claims, 25 Drawing Sheets

(56) References Cited

U.S. PATENT DOCUMENTS

| | | | |
|---|---|---|---|
| 8,981,106 B2* | 3/2015 | Maeda | A61K 31/44 546/297 |
| 8,993,541 B2* | 3/2015 | Maeda | A61K 31/44 514/64 |
| 9,480,694 B2* | 11/2016 | Zebala | |
| 2004/0116479 A1 | 6/2004 | Haviv et al. | |
| 2006/0063790 A1 | 3/2006 | Gillman et al. | |
| 2007/0015734 A1 | 1/2007 | McElroy et al. | |
| 2009/0163463 A1 | 6/2009 | Bruce et al. | |
| 2010/0210593 A1* | 8/2010 | Maeda | A61K 31/44 514/64 |
| 2012/0046243 A1* | 2/2012 | Maeda | A61K 31/44 514/64 |
| 2014/0206647 A1* | 7/2014 | Maeda | A61K 31/44 514/64 |
| 2014/0256678 A1 | 9/2014 | Maeda et al. | |
| 2015/0038461 A1 | 2/2015 | Zebala et al. | |
| 2017/0014435 A1* | 1/2017 | Zebala | A61K 31/69 |

FOREIGN PATENT DOCUMENTS

| | | |
|---|---|---|
| JP | 2008-511675 A | 4/2008 |
| JP | 2010-510272 A | 4/2010 |
| JP | 2013-536234 A | 9/2013 |
| WO | WO 1993/010102 A1 | 5/1993 |
| WO | WO 2001/025242 A1 | 4/2001 |
| WO | WO 2002/053544 A1 | 7/2002 |
| WO | WO 2003/024448 A2 | 3/2003 |
| WO | WO 2006/028958 A2 | 3/2006 |
| WO | WO 2007/071358 A1 | 6/2007 |
| WO | WO 2008/061795 A2 | 5/2008 |
| WO | WO 2008/073936 A1 | 6/2008 |
| WO | WO 2008/123469 A1 | 10/2008 |
| WO | WO 2008/130320 A2 | 10/2008 |
| WO | WO 2009/016088 A1 | 2/2009 |
| WO | WO 2009/037503 A2 | 3/2009 |
| WO | WO 2009/071476 A1 | 6/2009 |
| WO | WO 2010/007382 A1 | 1/2010 |
| WO | WO 2010/032875 A2 | 3/2010 |
| WO | WO 2010/127978 A1 | 11/2010 |
| WO | WO 2011/025838 A1 | 3/2011 |
| WO | WO 2011/133888 A1 | 10/2011 |
| WO | WO 2012/027289 A1 | 3/2012 |

OTHER PUBLICATIONS

Beg et al., "An Essential Role for NF-κB in Preventing TNF-α-Induced Cell Death", Science, 1996, 782-784.
Berge et al., "Pharmaceutical Salts", J. Pharm. Sci., 1977, 66(1), 1-19.
Bulinski et al., "Overexpression of MAP4 Inhibits Organell Motility and Trafficking in Vivo", J. Cell Sci., 1997, 110, 3055-3064.
Donnelly et al., "Interleukin-8 and Development of Adult Respiratory Distress Syndrome in At-Risk Patient Groups", Lancet, 1993, 341, 643-647.
Gould, "Salt Selection for Basic Drugs", Intl. J. Pharmaceutics, 1986, 33(1-3), 201-217.
Haghnegandar et al., "The Tumorigenic and Angiogenic Effects of MGSA/GRO Proteins in Melanoma", J. Leukoc. Biology, 2000, 67(1), 53-62.
Inoue et al., "Interleukin 8 Expression Regulates Tumorigenicity and Metastases in Androgen-Independent Prostate Cancer", Clin. Cancer Res., 2000, 6, 2104-2119.
Lopes et al., "Assessment of Microtubule Stabilizers by Semiautomated In Vitro Microtubule Protein Polymerization and Mitotic Block Assays", Cancer Chemotherapy and Pharmacology, Nov. 1997, 41(1), 37-47.
Miller et al., "Biology and Biochemistry of the Chemokines: A Family of Chemotactic and Inflammatory Cytokines", Crit. Rev. Immunol., 1992, 12(2), 17-46.
Miller et al., Elevated Levels of NAP-1/Interleukin-8 are present in the Airspaces of Patients with the Adult Respiratory Distress Syndrome and are Associated with Increased Mortality, Am. Rev. Respir. Dis., 1992, 146(2), 427-432.
Muhlradt et al., "Epothilone B Stabilizaes Microtubuli of Macrophages Like Taxol Without Showing Taxol-Like Endotoxin Activity", Cancer Res., 1997, 57,3344-3346.
Nicolaou et al., "Synthesis of Epothilones A and B in Solid and Solution Phase", Nature, 1997, 387, 268-272.
Oppenheim et al., "Properties of the Novel Proinflammatory Supergene 'Intercrine' Cytokine Family", Annu. Rev. Immunol., 1991, 9, 617-648.
Panda et al., "Differential Effects of Vinblastine on Polymerization and Dynamics at Opposite Microtubule Ends", J. Biol. Chem., 1996, 271(47), 29807-29812.
Panda et al., "Stabilization of Microtubule Dynamics by Estramustine by Binding to a Novel Site in Tubulin: A Possible Mechanistic Basis for its Antitumor Action", Proc. Natl. Acad. Sci. USA, 1997, 94, 10560-10564.
Seitz et al., "Enhanced Production of Neutrophil-Activating Peptide-1/Interleukin-8 in Rheumatoid Arthritis", J. Clin. Invest., 1991, 87, 463-469.
Service, "Tumor Killer Made; How Does It Work?", Science, 1996, 274, 1 page.
Strieter et al., "The Functional Role of the ELR Motif in CXC Chemokine-mediated Angiogenesis", 1995, 270(45), 27348-27357.
Vasquez et al., "Nanomolar Concentrations of Nocodazole Alter Microtubule Dynamic Instability In Vivo and In Vitro", Mol. Biol. Cell., 1997, 8, 973-985.
Yoneda et. al., "Expression of Angiogenesis-Related Genes and Progression of Human Ovarian Carcinomas in Nude Mice", J. Nat.Cancer Inst., 1998, 90, 447-454.
Yuen et al., "Deprotection of pinacolyl boronate esters via hydrolysis of intermediate potassium trifluoroborates", Tetrahedron Letters, 2005, 46, 7899-7903.
R.L. Auten et al.; 299; The Journal of Pharmacology and Experimental Therapeutics; 90-95; 2001.
R. Bertini et al.; 101 PNAS; 11791-11796; 2004.
C. Bizzari et al.; 112 Pharmacology & Therapeutics; 139-149; 2006.
R.W. Chapman et al.; 121 Pharmacology & Therapeutics; 55-68; 2009.
J.P. Jacobs et al.; 62 Arthritis & Rheumatism; 1921-1932; 2010.
P.L. Podolin et al.; 169 The Journal of Immunology; 6435-6444; 2002.
K. Reich et al.; 116 The Journal of Investigative Dermatology; 319-329; 2001.
Silverman, R.; "The Organic Chemistry of Drug Design and Drug Action," 2004, Elsevier, pp. 29-32.
Cutshall et al.; "Nicotinanilides as Inhibitors of Neutroophil Chemotaxis"; Bioorg. Med. Chem. Letter; 2002, vol. 12, pp. 1517-1520.
Ross; CAPLUS; accession No. 1967:443649; 2013; 1 page.
Winkelmann et al.; CAPLUS; accession No. 1978:443236; 2013; 1 page.
Prachayasittikul et al.; CAPLUS; accession No. 1986:148697; 2013; 1 page.
Sasse et al.; CAPLUS; accession No. 1988:454789; 2013; 5 pages.
Jackman et al.; CAPLUS; accession No. 1988:528959; 2013; 1 page.
Busch-Petersen; "Small Molecule Antagonists of the CXCR2 and CXCR1 Chemokine Receptors as Therapeutic Agents for the Treatment of Inflammatory Diseases" Curr Topics Med Chem. vol. 6 No. 13; 2006; p. 1345-1352.
Nicholls et al.; "Identification of a Putative Intracellular Allosteric Antagonist Binding-Site in the CXC Chemokine Receptors 1 and 2" Mol. Pharm. vol. 74 No. 5; 2008; p. 1193-1202.
Cutshall et al.; "Nicotinamide N-Oxides as CXCR2 Antagonists"; Bioorganic Medicinal Chem. Lett. 11; 2001; p. 1951-1954.
Maeda et al.; "Nicotinamide Glycolates Antagonize CXCR2 Activity through an Intracellular Mechanism"; J. Pharm. Exp. Ther. Vo. 332 No. 1; 2010; p. 145-152.
Thorarensen et al.; CAPLUS; accession No. 2004:182843; 2012; 6 pages.

(56) References Cited

OTHER PUBLICATIONS de Kruijf et al.; "Nonpeptidergic allosteric antagonists differently bind to the CXCR2 chemokine receptor"; J. Pharm. Exp. Ther. vol. 329 No. 2; 2009; p. 783-790.
Cutshall et al.; CAPLUS; accession No. 2002:521710; 2013; 2 pages.
International Patent Application No. PCT/US2013/053376; Int'l Preliminary Report on Patentability; dated Feb. 11, 2016; 7 pages.
Y.S. Yoon et al.; 9 The International Journal of Tuberculosis and Lung Disease; 2005; p. 1215-1219.
Z. Wang et al.; 19 Drug Delivery Today; 2014; p. 145-150.
U.K. Marelli et al.; 3 Frontiers in Oncology; 2013; p. 1-12.
T.M. Cunha et al.; 154 British Journal of Pharmacology; 2008; p. 460-470.
D.R. Nagarkar et al.; 183 The Journal of Immunology; 2009; p. 6698-6707.
J. Belperio et al.; 110 The Journal of Clinical Investigation; 2002; p. 1703-1716.
R.D. Sue et al.; 172 Journal of Immunology; 2004; p. 3860-3868.

* cited by examiner

METHOD FOR TREATING CANCER USING CHEMOKINE ANTAGONISTS

GOVERNMENT RIGHTS

"This invention was made with government support under Grant Number HL072614 awarded by the National Institutes of Health. The government has certain rights in the invention."

The disclosure of U.S. patent application Ser. No. 15/279,361 filed on Sep. 28, 2016, U.S. patent application Ser. No. 14/610,960 filed on Jan. 30, 2015, now issued U.S. Pat. No. 9,480,694, and U.S. patent application Ser. No. 13/957,665, filed Aug. 2, 2013, now issued U.S. Pat. No. 8,969,365, are incorporated herein by reference in their entirety.

TECHNICAL FIELD

The present disclosure provides a method of treating cancer using a pyrimidinecarboxamide compound, and pharmaceutical compositions for inhalation that include these compounds.

BACKGROUND

Chemokines are chemotactic proteins that have the potential to attract macrophages, T-cells, eosinophils, basophils, neutrophils and endothelial cells to sites of inflammation and tumor growth. Chemokines are typically low molecular mass (7-9 kD) proteins that can be divided into four sub-families: CC (or β-chemokines), CXC, C (or γ-chemokines) and CX3C (or δ-chemokines). The chemokines are categorized through their primary amino acid structure. The CXC subfamily is characterized by two conserved Cys residues (C) near the N-terminus and separated by an amino acid (X). The CXC-chemokines include, for example, interleukin-8 (IL-8), neutrophil-activating protein-1 (NAP-1), neutrophil-activating protein-2 (NAP-2), GROα, GROβ, GROγ, ENA-78, GCP-2, IP-10, MIG and PF4. The CXC subfamily of chemokines is further characterized by the presence or absence of a specific amino acid sequence, glutamic acid-leucine-arginine (or ELR for short) immediately before the first Cys residue of the CXC motif. Those chemokines with the ELR motif (ELRCXC) are important for the recruitment and activation of neutrophils to sites of inflammation. GROα and IL-8 are examples of ELRCXC chemokines.

The CXC-chemokines mediate their chemotactic activity through interaction with the chemokine receptors CXCR1 and CXCR2. CXCR1 binds IL-8 and GCP-2 with high affinity while CXCR2 binds all ELRCXC chemokines with high affinity.

Since CXC-chemokines promote the accumulation and activation of neutrophils, CXC-chemokines have been implicated in a wide range of acute and chronic inflammatory disorders including COPD, psoriasis and rheumatoid arthritis. (Baggiolini, 1992, *FEBS Lett*, 307:97; Miller, 1992. *Crit Rev Immuno.*, 12:17; Oppenheim, 1991, *Annu Rev Immunol*, 9:617; Seitz, 1991, *J Clin Invest*, 87:463; Miller, 1992, *Am Rev Respir Dis*, 146:427; Donnely, 1998, *Lancet*, 341:643).

ELRCXC chemokines, including IL-8, GROα, GROβ, GROγ, NAP-2, and ENA-78 (Strieter, 1995, *J Biol Chem*, 270:27348-57), have also been implicated in the induction of tumor angiogenesis (new blood vessel growth). Angiogenic activity is due to ELRCXC-chemokine binding to, and activation of CXCR2, and possibly CXCR1 for IL-8, expressed on the surface of vascular endothelial cells (ECs) in surrounding vessels.

Many different types of tumors have been shown to produce ELRCXC chemokines. Chemokine production has been correlated with a more aggressive phenotype (Inoue, 2000, *Clin Cancer Res*, 6:2104-2119) and poor prognosis (Yoneda, 1998, *J Nat Cancer Inst*, 90:447-54). Chemokines are potent chemotactic factors and the ELRCXC chemokines, in particular, have been shown to induce EC chemotaxis. Thus, these chemokines are thought to induce chemotaxis of endothelial cells toward their site of production in the tumor. This may be a critical step in the induction of angiogenesis by the tumor. Inhibitors of CXCR2 or dual inhibitors of CXCR2 and CXCR1 will inhibit the angiogenic activity of the ELRCXC chemokines and therefore block the growth of the tumor. This anti-tumor activity has been demonstrated for antibodies to IL-8 (Arenberg, 1996, *J Clin Invest*, 97:2792-802), ENA-78 (Arenberg, 1998, *J Clin Invest*, 102:465-72), and GROα (Haghnegandar, 2000, *J Leukoc Biology*, 67:53-62).

Therefore, there is a need in the art to find CXCR1/2 inhibitor compounds and modulator compounds that can be used as pharmaceutical compounds. There remains a need for compounds that are capable of modulating activity at CXC-chemokine receptors. For example, conditions associated with an increase in IL-8 production (which is responsible for chemotaxis of neutrophil and T-cell subsets into the inflammatory site and growth of tumors) would benefit by compounds that are inhibitors of IL-8 receptor binding. The present disclosure was made to satisfy this need.

SUMMARY

The present disclosure further provides the compound having the formula SX-682

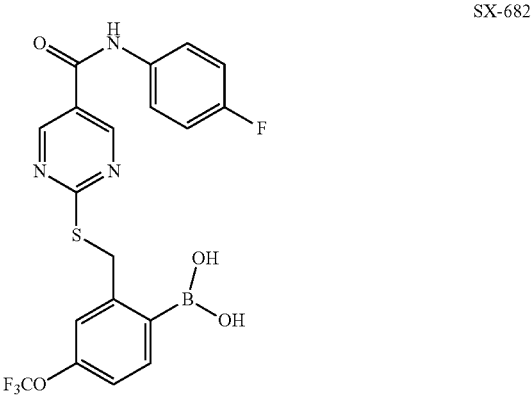 [SMILES: O=C(Nc1ccc(F)cc1)c1cnc(SCc2cc(OC(F)(F)F)ccc2B(O)O)nc1]

The present disclosure further provides a pharmaceutical composition comprising the compound having the formula SX-682, or a pharmaceutically acceptable salt, or solvate thereof and a pharmaceutically acceptable carrier. In certain embodiments, this disclosure provides SX-682 as a novel compound that is a CXC chemokine-modulator, pharmaceutical compositions comprising SX-682, and methods of treatment, prevention, inhibition, or amelioration of one or more diseases associated with CXC chemokine mediation using SX-682 and compositions disclosed herein.

The present disclosure provides a method for treating a disease or disorder selected from the group consisting of pain (e.g., acute pain, acute inflammatory pain, chronic inflammatory pain, and neuropathic pain), acute inflammation, chronic inflammation, rheumatoid arthritis, psoriasis, atopic dermatitis, bronchopulmonary dysplasia, COPD, adult respiratory disease, arthritis, inflammatory bowel disease, Crohn's disease, ulcerative colitis, septic shock, endotoxic shock, gram negative sepsis, toxic shock syndrome, stroke, ischemia reperfusion injury, renal reperfusion injury, glomerulonephritis, thrombosis, Alzheimer's disease, graft vs. host reaction (i.e., graft-versus-host disease), allograft rejections (e.g., acute allograft rejection, and chronic allograft rejection), malaria, acute respiratory distress syndrome, delayed type hypersensitivity reaction, atherosclerosis, cerebral ischemia, cardiac ischemia, osteoarthritis, multiple sclerosis, restinosis, angiogenesis, angiogenesis associated with tumor growth, osteoporosis, gingivitis, respiratory viruses, herpes viruses, hepatitis viruses, HIV, Kaposi's sarcoma associated virus (i.e., Kaposi's sarcoma), meningitis, cystic fibrosis, pre-term labor, cough, pruritis, multi-organ dysfunction, trauma, strains, sprains, contusions, psoriatic arthritis, herpes, encephalitis, CNS vasculitis, traumatic brain injury, systemic tumors, CNS tumors, tumors dependent on angiogenesis for growth, leukopenia and neutropenia, chemotherapy-induced leukopenia and neutropenia, opportunistic infections associated with neutropenia or leukopenia, subarachnoid hemorrhage, post-surgical trauma, interstitial pneumonitis, hypersensitivity, crystal induced arthritis, acute pancreatitis, chronic pancreatitis, acute alcoholic hepatitis, necrotizing enterocolitis, chronic sinusitis, angiogenic ocular disease, ocular inflammation, retinopathy of prematurity, diabetic retinopathy, macular degeneration with the wet type preferred, corneal neovascularization, polymyositis, vasculitis, acne, gastric ulcers, duodenal ulcers, celiac disease, esophagitis, glossitis, airflow obstruction, airway hyperresponsiveness (i.e., airway hyperreactivity), bronchiectasis, bronchiolitis, bronchiolitis obliterans, chronic bronchitis, cor pulmonae, dyspnea, emphysema, hypercapnea, hyperinflation, hypoxemia, hyperoxia-induced inflammations, hypoxia, surgical lung volume reduction, pulmonary fibrosis, pulmonary hypertension, right ventricular hypertrophy, peritonitis associated with continuous ambulatory peritoneal dialysis (CAPD), granulocytic ehrlichiosis, sarcoidosis, small airway disease, ventilation-perfusion mismatching, wheeze, colds, gout, alcoholic liver disease, lupus, burn therapy (i.e., the treatment of burns), periodontitis, cancer, transplant reperfusion injury, and early transplantation rejection (e.g., acute allograft rejection) in a patient in need of such treatment, comprising administering an effective amount of the compound having the formula SX-682.

The present disclosure further provides a method for treating a patient with a cancer, comprising administering to the patient in need thereof a pharmaceutical composition comprising a therapeutically effective amount of a compound of formula SX-517, SX-576, or SX-682, or a pharmaceutically acceptable salt or solvate thereof, and performing at least one of (a), (b), (c) and (d), wherein (a) comprises assaying serum levels of CXCR1 and/or CXCR2 ligands in the patient prior to the treatment, (b) comprises assaying serum levels of CXCR1 and/or CXCR2 ligands in the patient after the treatment, (c) comprises assaying serum levels of myeloid derived suppressor cells (MDSCs) and/or neutrophils in the patient prior to the treatment, and (d) comprises assaying serum levels of MDSCs or neutrophils in the patient after the treatment. The method further comprises administering an anticancer therapy, e.g., wherein the anticancer therapy is a chemotherapy, including wherein carboplatin is administered to the patient. The method further comprises wherein the anticancer therapy is radiation therapy.

In one embodiment the method uses the compound of formula SX-682 and the cancer is selected from cancers of the prostate, colorectum, pancreas, cervix, stomach, endometrium, brain, liver, bladder, ovary, testis, head, neck, skin, mesothelial lining, blood, esophagus, breast, muscle, connective tissue, lung, adrenal gland, thyroid, kidney, lymphoid system, bone marrow or bone, glioblastoma, mesothelioma, renal cell carcinoma, gastric carcinoma, sarcoma, choriocarcinoma, cutaneous basocellular carcinoma, and testicular seminoma.

In another embodiment the method uses the compound of formula SX-682 and the cancer is selected from cancers of the prostate, pancreas, stomach, brain, liver, head, neck, skin, blood, breast, lung, glioblastoma, and mesothelioma.

In another embodiment the method uses the compound of formula SX-682 and the cancer is breast cancer, preferably by oral administration. The breast cancer therapy further comprises administering a platinum chemotherapy.

In another embodiment the method uses the compound of formula SX-682 and the cancer is a melanoma, preferably by oral administration. The melanoma cancer treatment further comprises administering a platinum chemotherapy.

In another embodiment, the method uses the compound of formula SX-517, SX-576, or SX-682, for treating a lung cancer, preferably by oral administration.

In another embodiment, the method uses the compound has the structure of formula SX-682 for treating a prostate cancer, preferably by oral administration.

In another embodiment, the method uses the compound of formula SX-517, SX-576, or SX-682, for treating a cancer, wherein the cancer is a glioblastoma, preferably by oral administration. The glioblastoma treatment further comprises administering temozolomide.

In another embodiment, the method uses the compound of formula SX-517, SX-576, or SX-682, for treating pancreatic cancer, preferably by oral administration.

The present disclosure further provides a method for treating a patient with a cancer, comprising administering to the patient in need thereof a pharmaceutical composition comprising a therapeutically effective amount of a compound having a structure selected from the group consisting of formulas SX-517, SX-576, and SX-682,

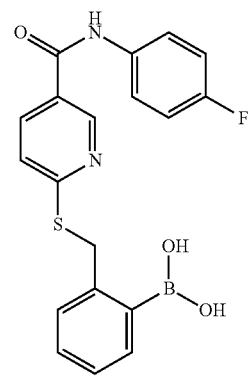

SX-517

-continued

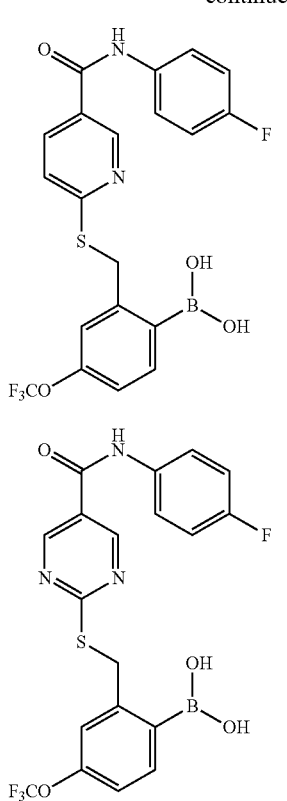

SX-576

SX-682 or a pharmaceutically acceptable salt or solvate thereof, wherein the cancer is a glioblastoma or a pancreatic cancer.

DETAILED DESCRIPTION OF ILLUSTRATIVE EMBODIMENTS

Definitions

Figure 1:
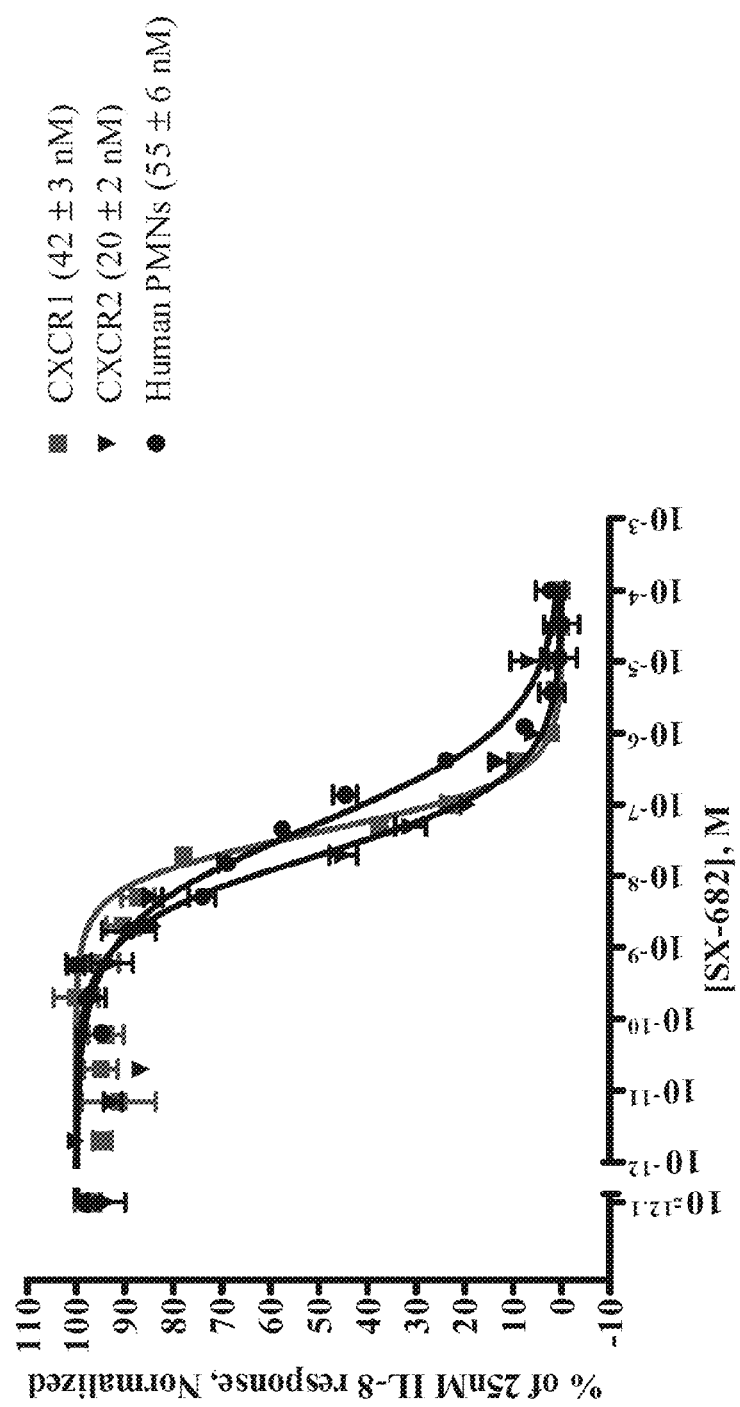
FIG. 1 shows that SX-682 inhibited CXCL8-mediated intracellular calcium flux in isolated human neutrophils ('Human PMNs'), RBL cells stably transfected with CXCR1 (legend 'CXCR1'), and RBL cells stably transfected with CXCR2 (legend 'CXCR2'). Mean (n=4, ±SE) $IC_{50}$ values for SX-682 in each cell system are in parentheses in the legend.

When any substituent or variable occurs more than one time in any moiety, its definition on each occurrence is independent of its definition at every other occurrence. Also, combinations of substituents and/or variables are permissible only if such combinations result in stable compounds.

Unless indicated otherwise, the following definitions apply throughout the present specification and claims. These definitions apply regardless of whether a term is used by itself or in combination with other terms. For example, the definition of "alkyl" also applies to the "alkyl" portion of the defined term "alkoxy".

"An effective amount" or a "therapeutically effective amount" means to describe an amount of compound of the present disclosure or another agent effective to treat a mammal (e.g., a human) having a disease or CXC chemokine-mediated condition, and thus producing the desired therapeutic effect.

"At least one" means one or more (e.g., 1-3, 1-2, or 1).

"Composition" includes a product comprising the specified ingredients in the specified amounts, as well as any product that results, directly or indirectly, from combination of the specified ingredients in the specified amounts.

"In combination with" as used to describe the administration of SX-682 with other medicaments in the methods of treatment of this invention, means-that SX-682 and the other medicaments are administered sequentially or concurrently in separate dosage forms, or are administered concurrently in the same dosage form.

"Mammal" means a human or other mammal, or means a human being.

"Patient" includes both human and other mammals, preferably human.

"Prodrug" denotes a compound that is a drug precursor which, upon administration to a subject, undergoes chemical conversion by metabolic or chemical processes to yield SX-682 or a salt and/or solvate thereof. A discussion of pro-drugs is provided in Higuchi, *Pro-drugs as Novel Delivery Systems*, v. 14 of the A.C.S. Symp Series, and in Bioreversible Carriers in Drug Design, Roche, ed., Am Pharma Assoc, Pergamon Press, 1987, both of which are incorporated herein by reference.

"Alkyl" is a saturated or unsaturated, straight or branched, hydrocarbon chain. In various embodiments, the alkyl group has 1-18 carbon atoms, i.e. is a $C_1$-$C_{18}$ group, or is a $C_1$-$C_{12}$ group, a $C_1$-$C_6$ group, or a $C_1$-$C_4$ group. A lower alkyl group has 1-6 carbons. Independently, in various embodiments, the alkyl group has zero branches (i.e., is a straight chain), one branch, two branches, or more than two branches. Independently, in one embodiment, the alkyl group is saturated. In another embodiment, the alkyl group is unsaturated. In various embodiments, the unsaturated alkyl may have one double bond, two double bonds, more than two double bonds, and/or one triple bond, two triple bonds, or more than two triple bonds. Alkyl chains may be optionally substituted with 1 substituent (i.e., the alkyl group is mono-substituted), or 1-2 substituents, or 1-3 substituents, or 1-4 substituents, etc. The substituents may be selected from the group consisting of hydroxy, amino, alkylamino, boronyl, carboxy, nitro, cyano, and the like. When the alkyl group incorporates one or more heteroatoms, the alkyl group is referred to herein as a heteroalkyl group. When the substituents on an alkyl group are hydrocarbons, then the resulting group is simply referred to as a substituted alkyl. In various aspects, the alkyl group including substituents has less than 25, 24, 23, 22, 21, 20, 19, 18, 17, 16, 15, 14, 13, 12, 11, 10, 9, 8, or 7 carbons.

"Lower alkyl" means a group having about 1 to about 6 carbon atoms in the chain which chain may be straight or branched. Non-limiting examples of suitable alkyl groups include methyl, ethyl, n-propyl, isopropyl, n-butyl, t-butyl, n-pentyl, heptyl, nonyl, and decyl.

"Alkoxy" means an alkyl-O-group wherein alkyl is as defined above. Non-limiting examples of alkoxy groups include: methoxy, ethoxy, n-propoxy, isopropoxy, n-butoxy and heptoxy. The bond to the parent moiety is through the ether oxygen.

"Alkoxyalkyl" means an alkoxy-alkyl-group in which the alkoxy and alkyl are as previously described. Preferred alkoxyalkyl comprise a lower alkyl group. The bond to the parent moiety is through the alkyl.

"Alkylaryl" means an alkyl-aryl-group in which the alkyl and aryl are as previously described. Preferred alkylaryls comprise a lower alkyl group. The bond to the parent moiety is through the aryl.

"Aminoalkyl" means an $NH_2$-alkyl-group, wherein alkyl is as defined above, bound to the parent moiety through the alkyl group.

"Aryl" (sometimes abbreviated "Ar") is an aromatic carbocyclic hydrocarbon ring system. The ring system may be monocyclic or fused polycyclic (e.g., bicyclic, tricyclic, etc.). In one embodiment, the aryl group is monocyclic, and is preferably a $C_6$ ring system, i.e. a phenyl ring is a preferred aryl ring, where preferred bicyclic aryl rings are $C_8$-$C_{12}$, or $C_9$-$C_{10}$. A naphthyl ring, which has 10 carbon atoms, is a preferred polycyclic aryl ring. Unless otherwise indicated herein, the term "aryl" as used herein is meant to include aryl rings optionally substituted by one or more substituents selected from acyl (—C(O)—R), alkoxy (—O—R), alkyl, aryl, alkylamino (—N(H)—R and —N(R)R), alkylthio (—S—R), amino (—$NH_2$), azido (—$N_3$), boronyl (—B(R)R or —B(OH)$_2$ or —B(OR)$_2$), carboxy (—C(O)—OH), alkoxycarbonyl (—C(O)—OR), aminocarbonyl (—C(O)—$NH_2$), aminosulfonyl (—S(O)$_2$—$NH_2$), alkylaminocarbonyl (—C(O)—N(H)R and —C(O)—N(R)R), cyano, halo (fluoro, bromo, chloro, iodo), haloalkyl, haloalkoxy, heterocyclyl, heteroalkyl, hydroxyl (—OH), acyloxy (—O—C(O)—R), ketone (—C(O)—R), substituted halomethylketone (—C(O)—$CH_mX_n$, where m+n=3, X=F, Cl, Br), mercapto (—SH and —S—R) and nitro (—$NO_2$) where each R group is an alkyl group having less than about 12 carbons, preferably where the R group is a lower alkyl group. Non-limiting examples of suitable aryl groups include: phenyl, naphthyl, indenyl, tetrahydronaphthyl, indanyl, anthracenyl, and fluorenyl.

"Arylalkyl" refers to an alkyl group as defined substituted by one or more aryl groups as defined below. Phenyl and naphthyl are preferred aryl groups in an arylalkyl group. A preferred alkyl group is methyl, so that a preferred arylalkyl group is benzyl or benzyl having one or more substituents on the phenyl ring. Unless otherwise indicated, the term "arylalkyl" as used herein is meant to include arylalkyl groups wherein the aryl ring therein is optionally substituted by one or more substituents selected from acyl (—C(O)—R), alkoxy (—O—R), alkyl, aryl, alkylamino (—N(H)—R and —N(R)R), alkylthio (—S—R), amino (—$NH_2$), azido (—$N_3$), boronyl (—B(R)R or —B(OH)$_2$ or —B(OR)$_2$), carboxy (—C(O)—OH), alkoxycarbonyl (—C(O)—OR), aminocarbonyl (—C(O)—$NH_2$), aminosulfonyl (—S(O)$_2$—$NH_2$), alkylaminocarbonyl (—C(O)—N(H)R and —C(O)—N(R)R), cyano, halo (fluoro, bromo, chloro, iodo), haloalkyl, haloalkoxy, heterocyclyl, heteroalkyl, hydroxyl (—OH), acyloxy (—O—C(O)—R), ketone (—C(O)—R), substituted halomethylketone (—C(O)—$CH_mX_n$, where m+n=3, X=F, Cl, Br), mercapto (—SH and —S—R) and nitro (—$NO_2$) where each R is an alkyl group having less than about 12 carbons, preferably where the R group is a lower alkyl group.

"Arylalkyl" means an aryl-alkyl-group in which the aryl and alkyl are as previously described. Preferred arylalkyls comprise a lower alkyl group. Non-limiting examples of suitable aralkyl groups include benzyl, 2-phenethyl and napthalenylmethyl. The bond to the parent moiety is through the alkyl.

"Aryloxy" means an aryl-O-group in which the aryl group is as previously described. Non-limiting examples of suitable aryloxy groups include phenoxy and naphthoxy. The bond to the parent moiety is through the ether oxygen.

"Carboxyalkyl" means an HOOC-alkyl-group, wherein alkyl is as defined above, bound to the parent moiety through the alkyl group.

"Chemokine" means a protein molecule involved in chemotaxis.

A "chemokine-mediated disease" means a disease of which at least one element or cause is related to the regulation of a CXC chemokine.

"Commercially available chemicals" and the chemicals used in the Examples set forth herein may be obtained from standard commercial sources, where such sources include, for example, Acros Organics (Pittsburgh, Pa.), Sigma-Aldrich Chemical (Milwaukee, Wis.), Avocado Research (Lancashire, U.K.), Bionet (Cornwall, U.K.), Boron Molecular (Research Triangle Park, N.C.), Combi-Blocks (San Diego, Calif.), Eastman Organic Chemicals, Eastman Kodak Company (Rochester, N.Y.), Fisher Scientific Co. (Pittsburgh, Pa.), Frontier Scientific (Logan, Utah), ICN Biomedicals, Inc. (Costa Mesa, Calif.), Lancaster Synthesis (Windham, N.H.), Maybridge Chemical Co. (Cornwall, U.K.), Pierce Chemical Co. (Rockford, Ill.), Riedel de Haen (Hannover, Germany), Spectrum Quality Product, Inc. (New Brunswick, N.J.), TCI America (Portland, Oreg.), and Wako Chemicals USA, Inc. (Richmond, Va.).

"Compounds described in the chemical literature" may be identified through reference books and databases directed to chemical compounds and chemical reactions, as known to one of ordinary skill in the art. Suitable reference books and treatise that detail the synthesis of reactants useful in the preparation of compounds disclosed herein, or provide references to articles that describe the preparation of compounds disclosed herein, include for example, "Synthetic Organic Chemistry", John Wiley and Sons, Inc. New York; S. R. Sandler et al, "Organic Functional Group Preparations," $2^{nd}$ Ed., Academic Press, New York, 1983; H. O. House, "Modern Synthetic Reactions," $2^{nd}$ Ed., W. A. Benjamin, Inc. Menlo Park, Calif., 1972; T. L. Glichrist, "Heterocyclic Chemistry," $2^{nd}$ Ed. John Wiley and Sons, New York, 1992; J. March, "Advanced Organic Chemistry: reactions, Mechanisms and Structure," $5^{th}$ Ed., Wiley Interscience, New York, 2001; Specific and analogous reactants may also be identified through the indices of known chemicals prepared by the Chemical Abstract Service of the American Chemical Society, which are available in most public and university libraries, as well as through online databases (the American Chemical Society, Washington, D.C.). Chemicals that are known but not commercially available in catalogs may be prepared by custom chemical synthesis houses, where many of the standard chemical supply houses (e.g. those listed above) provide custom synthesis services.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. A multicyclic cycloalkyl substituent may include fused, Spiro, or bridged ring structures. Non-limiting examples of suitable monocyclic cycloalkyls include cyclopropyl, cyclobutyl, cyclopentyl, cyclohexyl, cycloheptyl and the like. Non-limiting examples of suitable multicyclic cycloalkyls include 1-decalin, norbornyl, adamantly and the like. Cycloalkyl substituents may be substituted or unsubstituted. In one embodiment, the cycloalkyl is unsubstituted. In another embodiment, the cycloalkyl is substituted with, e.g., 1 substituent (i.e., the cycloalkyl group is mono-substituted), or 1-2 substituents, or 1-3 substituents, or 1-4 substituents, etc. In one embodiment, the substituents that may be present on the cycloalkyl aliphatic ring are selected from acyl (—C(O)—R), alkoxy (—O—R), alkyl, aryl, alkylamino (—N(H)—R and —N(R)R), alkylthio (—S—R), amino (—NH$_2$), azido (—N$_3$), boronyl (—B(R)R or —B(OH)$_2$ or —B(OR)$_2$), carboxy (—C(O)—OH), alkoxycarbonyl (—C(O)—OR), aminocarbonyl (—C(O)—NH$_2$), aminosulfonyl (—S(O)$_2$—NH$_2$), alkylaminocarbonyl (—C(O)—N(H)R and —C(O)—N(R)R), cyano, halo (fluoro, bromo, chloro, iodo), haloalkyl, haloalkoxy, heterocyclyl, heteroalkyl, hydroxyl (—OH), acyloxy (—O—C(O)—R), ketone (—C(O)—R), substituted halomethylketone (—C(O)—CH$_m$X$_n$, where m+n=3, X=F, Cl, Br), mercapto (—SH and —S—R) and nitro (—NO$_2$). In one aspect the R group in the above substituents is an alkyl group having less than about 12 carbons, while in another aspect the R group is a lower alkyl group.

"Cycloalkylalkyl" means a cycloalkyl group bound to the parent moiety through an alkyl group. Non-limiting examples include: cyclopropylmethyl and cyclohexylmethyl.

"Cycloalkylaryl" means a cycloalkyl group bound to the parent moiety through an aryl group. Non-limiting examples include: cyclopropylphenyl and cyclohexylphenyl.

"Effective amount" or "therapeutically effective amount" is meant to describe an amount of compound or a composition of the present disclosure effective in decreasing or increasing (i.e., modulating) the action of a CXC chemokine at a CXC chemokine receptor and thus producing the desired therapeutic effect in a suitable patient.

"Fluoroalkoxy" means an alkoxy group as defined above wherein one or more hydrogen atoms on the alkoxy is or are replaced by a fluoro group.

"Fluoroalkyl" means an alkyl group as defined above wherein one or more hydrogen atoms on the alkyl are replaced by a fluoro group.

"Halo" means fluoro, chloro, bromo, or iodo groups. Preferred are fluoro, chloro or bromo, and more preferred are fluoro and chloro.

"Halogen" means fluorine, chlorine, bromine, or iodine. Preferred are fluorine, chlorine and bromine.

"Heteroalkyl" is a saturated or unsaturated, straight or branched, chain containing carbon and at least one heteroatom. The heteroalkyl group may, in various embodiments, have on heteroatom, or 1-2 heteroatoms, or 1-3 heteroatoms, or 1-4 heteroatoms. In one aspect the heteroalkyl chain contains from 1 to 18 (i.e., 1-18) member atoms (carbon and heteroatoms), and in various embodiments contain 1-12, or 1-6, or 1-4 member atoms. Independently, in various embodiments, the heteroalkyl group has zero branches (i.e., is a straight chain), one branch, two branches, or more than two branches. Independently, in one embodiment, the heteroalkyl group is saturated. In another embodiment, the heteroalkyl group is unsaturated. In various embodiments, the unsaturated heteroalkyl may have one double bond, two double bonds, more than two double bonds, and/or one triple bond, two triple bonds, or more than two triple bonds. Heteroalkyl chains may be substituted or unsubstituted. In one embodiment, the heteroalkyl chain is unsubstituted. In another embodiment, the heteroalkyl chain is substituted. A substituted heteroalkyl chain may have 1 substituent (i.e., by monosubstituted), or may have 1-2 substituents, or 1-3 substituents, or 1-4 substituents, etc. Exemplary heteroalkyl substituents include esters (—C(O)—O—R) and carbonyls (—C(O)—).

"Heterocyclic" (or "heterocycloalkyl" or "heterocyclyl") refers to a non-aromatic saturated monocyclic or multicyclic ring system comprising 3 to 10 ring atoms (e.g., 3 to 7 ring atoms), or 5 to 10 ring atoms, in which one or more of the atoms in the ring system is an element other than carbon, for example nitrogen, oxygen or sulfur, alone or in combination. There are no adjacent oxygen and/or sulfur atoms present in the ring system. Examples of heterocyclics or heterocycloalkyls include rings having 5 to 6 ring atoms. The prefix aza, oxa or thia before the heterocyclic or heterocycloalkyl root name means that at least a nitrogen, oxygen or sulfur atom, respectively, is present as a ring atom. The nitrogen or sulfur atom of the heterocyclic or heterocycloalkyl can be optionally oxidized to the corresponding N-oxide, S-oxide or S,S-dioxide. Any nitrogen atoms may be optionally quaternized. Non-limiting examples of monocyclic heterocyclic or heterocycloalkyl rings include: piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophen-yl, and tetrahydrothiopyranyl The heterocyclyl may be unsubstituted or substituted. In one embodiment, the heterocyclyl is unsubstituted. In another embodiment, the heterocyclyl is substituted. The substituted heterocyclyl ring may contain 1 substituent, or 1-2 substituents, or 1-3 substituents, or 1-4 substituents, etc. In one embodiment, the substituents that may be present on the heterocyclyl ring are selected from acyl (—C(O)—R), alkoxy (—O—R), alkyl, aryl, alkylamino (—N(H)—R and —N(R)R), alkylthio (—S—R), amino (—NH$_2$), azido (—N$_3$), boronyl (—B(R)R or —B(OH)$_2$ or —B(OR)$_2$), carboxy (—C(O)—OH), alkoxycarbonyl (—C(O)—OR), aminocarbonyl (—C(O)—NH$_2$), aminosulfonyl (—S(O)$_2$—NH$_2$), alkylaminocarbonyl (—C(O)—N(H)R and —C(O)—N(R)R), cyano, halo (fluoro, bromo, chloro, iodo), haloalkyl, haloalkoxy, heterocyclyl, heteroalkyl, hydroxyl (—OH), acyloxy (—O—C(O)—R), ketone (—C(O)—R), substituted halomethylketone (—C(O)—CH$_m$X$_n$, where m+n=3, X=F, Cl, Br), mercapto (—SH and —S—R) and nitro (—NO$_2$). In one aspect, the R group which is, or is part of the substituent attached to the heterocyclic ring is an alkyl group having less than about 12 carbons, while in another aspect the R group is a lower alkyl group.

"Heterocycloalkylalkyl" means a heterocycloalkyl-alkyl group, wherein said heterocycloalkyl and said alkyl are as defined above, bound to a parent moiety through the alkyl group.

"Heteroaryl" means an aromatic monocyclic or multicyclic ring system comprising 5 to 14 ring atoms, or 5 to 10 ring atoms, in which one or more of the ring atoms is an element other than carbon, for example nitrogen, oxygen or sulfur, alone or in combination. Heteroaryls can contain 5 to 6 ring atoms. The prefix aza, oxa or thio before the heteroaryl root name means that at least a nitrogen, oxygen or sulfur atom respectively, is present as a ring atom. A nitrogen atom of a heteroaryl can be optionally oxidized to the corresponding N-oxide. Any nitrogen atoms may be optionally quaternized. Non-limiting examples of heteroaryls include: pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, and benzothiazolyl. The heteroaryl may be unsubstituted or substituted. In one embodiment, the heteroaryl is unsubstituted. In another embodiment, the heteroaryl is substituted. The substituted heteroaryl ring may contain 1 substituent, or 1-2 substituents, or 1-3 substituents, or 1-4 substituents, etc. In one embodiment, the substituents that may be present on the heteroaryl ring are selected from acyl (—C(O)—R), alkoxy (—O—R), alkyl, aryl, alkylamino (—N(H)—R and —N(R)R), alkylthio (—S—R), amino (—NH$_2$), azido (—N$_3$), boronyl (—B(R)R or —B(OH)$_2$ or —B(OR)$_2$), carboxy (—C(O)—OH), alkoxycarbonyl (—C(O)—OR), aminocarbonyl (—C(O)—NH$_2$), aminosulfonyl (—S(O)$_2$—NH$_2$), alkylaminocarbonyl (—C(O)—N(H)R and —C(O)—N(R)R), cyano, halo (fluoro, bromo, chloro, iodo), haloalkyl, haloalkoxy, heterocyclyl, heteroalkyl, hydroxyl (—OH), acyloxy (—O—C(O)—R), ketone (—C(O)—R), substituted halomethylketone (—C(O)—CH$_m$X$_n$, where m+n=3, X=F, Cl, Br), mercapto (—SH and —S—R) and nitro (—NO$_2$). In one aspect, the R group which is, or is part of the substituent attached to the heteroaryl ring is an alkyl group having less than about 12 carbons, while in another aspect the R group is a lower alkyl group.

"Heteroarylkyl" or "heteroarylalkyl" means a heteroarylalkyl-group, in which the heteroaryl and alkyl are as previously described. Preferred heteroaralkyls can contain a lower alkyl group. Non-limiting examples of suitable aralkyl groups include pyridylmethyl, 2-(furan-3-yl)ethyl and quinolin-3-ylmethyl. The bond to the parent moiety is through the alkyl.

"Hydroxyalkyl" means an HO-alkyl-group, in which alkyl is previously defined. Preferred hydroxyalkyls contain lower alkyl. Non-limiting examples of suitable hydroxyalkyl groups include hydroxymethyl and 2-hydroxy ethyl.

"Hydrate" is a solvate wherein the solvent molecule is H$_2$O.

"Solvate" means a physical association of a compound of this disclosure with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like.

Examples of "disease modifying antirheumatic drugs" (i.e., DMARDs) include, for example, methotrexate, aminopterin, sulfasalzine, leflunomide, TNFa directed agents (e.g., infliximab, etanercept, and adalimumab), IL-1 directed agents (e.g., anakinra) B cell directed agents (e.g., rituximab), T cell directed agents (e.g., alefacept, efalizumab, and CTLA4-lg), TNFa-converting enzyme inhibitors, interleukin-1 converting enzyme is inhibitors, and p38 kinase inhibitors.

The term "other classes of compounds indicated for the treatment of rheumatoid arthritis", as used herein, unless indicated otherwise, means: compounds selected from the group consisting of: IL-1 directed agents (e.g., anakinra); B cell directed agents (e.g., rituximab); T cell directed agents (e.g., alefacept, efalizumab, and CTLA4-lg), TNFa-converting enzyme inhibitors, interleukin-1 converting enzyme inhibitors, and p38 kinase inhibitors.

The compound having the formula SX-682 forms salts that are also within the scope of this disclosure. Reference to the compound having the formula SX-682 herein is understood to include reference to salts thereof, unless otherwise indicated. The term "salt(s)", as employed herein, denotes acidic salts formed with inorganic and/or organic acids, as well as basic salts formed with inorganic and/or organic bases. The salts can be pharmaceutically acceptable (i.e., non-toxic, physiologically acceptable) salts, although other salts are also useful. Salts of the compound having the formula SX-682 may be formed, for example, by reacting it with an amount of acid or base, such as an equivalent amount, in a medium such as one in which the salt precipitates or in an aqueous medium followed by lyophilization.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxy ethanesulfonates, lactates, maleates, methanesulfonates, 2-napthalenesulfonates, nicotinates, nitrates, oxalates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates) undecanoates, and the like. Additionally, acids which are generally considered suitable for the formation of pharmaceutically useful salts from basic pharmaceutical compounds are discussed, for example, by Berge, 1977, *J Pharma Sci*, 66:1-19; Gould, 1986, *Int'l J Pharmaceutics*, 33:201-17; Anderson, The Practice of Medicinal Chemistry (1996), Acad Press, New York; and in The Orange Book (Food & Drug Administration, Washington, D.C.). These disclosures are incorporated herein by reference herein.

Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like. Basic nitrogen-containing groups may be quarternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl, and stearyl chlorides, bromides and iodides), aryalkyl halides (e.g., benzyl and phenethyl bromides), and others.

All such acid and base salts are intended to be pharmaceutically acceptable salts within the scope of the disclosure and all acid and base salts are considered equivalent to the free forms of the corresponding compounds for purposes of the disclosure.

The compound having the formula SX-682 can exist in unsolvated and solvated forms, including hydrated forms. In general, the solvated forms, with pharmaceutically acceptable solvents such as water, ethanol and the like, are equivalent to the unsolvated forms for the purposes of this disclosure.

The compound having the formula SX-682 and salts, solvates and prodrugs thereof, may exist in their tautomeric form (for example, as an amide or imino ether). All such tautomeric forms are contemplated herein as part of the present disclosure.

Also within the scope of the present disclosure are polymorphs of the compounds of this disclosure (i.e., polymorphs of the compound having the formula SX-682 are within the scope of this disclosure).

Prodrugs of the compound having the formula SX-682 or pharmaceutically acceptable salts or solvates thereof are within the scope of this disclosure.

All stereoisomers (for example, geometric isomers, optical isomers and the like) of the compound having the formula SX-682 (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this disclosure. Individual stereoisomers of the compounds of this disclosure may, for example, be substantially free of other isomers, or may be admixed, for example, as racemates or with all other, or other selected, stereoisomers. The chiral centers of the compounds herein can have the S or R configuration as defined by the IUPAC 1974 Recommendations. The use of the terms "salt", "solvate", "prodrug" and the like, is intended to equally apply to the salt, solvate and prodrug of enantiomers, stereoisomers, rotamers, tautomers, racemates or prodrugs of the disclosed compounds.

Classes of compounds that can be used as the chemotherapeutic agent (antineoplastic agent) include: alkylating agents, antimetabolites, natural products and their derivatives, hormones and steroids (including synthetic analogs), and synthetics. Examples of compounds within these classes are given below.

Alkylating agents (including nitrogen mustards, ethylenimine derivatives, alkyl sulfonates, nitrosoureas and triazenes): uracil mustard, chlormethine, cyclophosphamide, ifosfamide, melphalan, chlorambucil, pipobroman, triethylene-melamine, triethylenethiophos-phoramine, busulfan, carmustine, lomustine, streptozocin, dacarbazine, and temozolomide.

Antimetabolites (including folic acid antagonists, pyrimidine analogs, purine analogs and adenosine deaminase inhibitors): methotrexate, aminopterin, 5-fluorouracil, floxuridine, cytarabine, 6-mercaptopurine, 6-thioguanine, fludarabine phosphate, pentostatine, and gemcitabine.

Natural products and their derivatives (including vinca alkaloids, antitumor antibiotics, enzymes, lymphokines and epipodophyllotoxins): v inblastine, vincristine, vindesine, bleomycin, dactinomycin, daunorubicin, doxorubicin, epirubicin, idarubicin, paclitaxel (TAXOL®), mithramycin, deoxycoformycin, mitomycin-C, L-asparaginase, interferons (especially IFN-γ), etoposide, and teniposide.

Hormones and steroids (including synthetic analogs): 17α-ethinylestradiol, diethylstilbestrol, testosterone, prednisone, fluoxymesterone, dromostanolone propionate, testolactone, megestrolacetate, tamoxifen, methylprednisolone, methyltestosterone, prednisolone, triamcinolone, chlorotrianisene, hydroxyprogesterone, a minoglutethimide, estramustine, medroxyprogesteroneacetate, leuprolide, flutamide, toremifene, zoladex.

Synthetics (including inorganic complexes such as platinum coordination complexes): cisplatin, carboplatin, hydroxyurea, amsacrine, procarbazine, mitotane, mitoxantrone, levamisole, and hexamethylmelamine.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR), e.g., 2008 edition (Thomson P D R, Montvale, N.J. 07645); the disclosure of which is incorporated herein by reference herein.

As used herein, a microtubule affecting agent is a compound that interferes with cellular mitosis, i.e., having an anti-mitotic effect, by affecting microtubule formation and/or action. Such agents can be, for instance, microtubule stabilizing agents or agents that disrupt microtubule formation.

Microtubule affecting agents useful in this disclosure are well known to those of skilled in the art and include, but are not limited to allocolchicine (NSC 406042), halichondrin B (NSC 609395), colchicine (NSC 757), colchicine derivatives (e.g., NSC 33410), dolastatin 10 (NSC 376128), maytansine (NSC 153858), rhizoxin (NSC 332598), paclitaxel (TAXOL®, NSC 125973), TAXOL® derivatives (e.g., derivatives (e.g., NSC 608832), thiocolchicine (NSC 361792), trityl cysteine (NSC 83265), vinblastine sulfate (NSC 49842), vincristine sulfate (NSC 67574), epothilone A, epothilone, and discodermolide (see Service, 1996, *Science*, 274:2009) estramustine, nocodazole, MAP4, and the like. Examples of such agents are also described in the scientific and patent literature, see, e.g., Bulinski, 1997, *J Cell Sci*, 110:3055-64; Panda, 1997, *Proc Natl Acad Sci USA*, 94:10560-64; Muhlradt, 1997, *Cancer Res*, 57:3344-46; Nicolaou, 1997, *Nature*, 387:268-72; Vasquez, 1997, *Mol Biol Cell*, 8:973-85; and Panda, 1996, *J Biol Chem*, 271:29807-12.

Particularly, agents can be compounds with paclitaxel-like activity. These include, but are not limited to paclitaxel and paclitaxel derivatives (paclitaxel-like compounds) and analogues. Paclitaxel and its derivatives are available commercially. In addition, methods of making paclitaxel and paclitaxel derivatives and analogues are well known to those of skilled in the art (see, e.g., U.S. Pat. Nos. 5,569,729; 5,565,478; 5,530,020; 5,527,924; 5,508,447; 5,489,589; 5,488,116; 5,484,809; 5,478,854; 5,478,736; 5,475,120; 5,468,769; 5,461,169; 5,440,057; 5,422,364; 5,411,984; 5,405,972; and 5,296,506, the disclosures of which are incorporated by reference herein).

Additional microtubule affecting agents can be assessed using one of many such assays known in the art, e.g., a semiautomated assay which measures the tubulin-polymerizing activity of paclitaxel analogs in combination with a cellular assay to measure the potential of these compounds to block cells in mitosis (see Lopes, 1997, *Cancer Chemother Pharmacol*, 41:37-47).

Therapeutic Activity

Modulators of neutrophil activity can have great therapeutic benefit in a number of indications. In disease states characterized by an improperly heightened neutrophil response, an inhibitor of neutrophil activity would be indicated. In patients suffering from, for example neutropenia, a neutrophil agonist or activator has clinical benefit. In vivo evaluation of two lead compounds SX-517 and SX-576 in the murine air-pouch model of inflammation, revealed that both inhibitory and agonist activity on neutrophils were achieved, depending on the dose given.

Methods of Treatment

One embodiment is directed to a pharmaceutical composition comprising SX-682 or a pharmaceutically acceptable salt or solvate thereof, in combination with a pharmaceutically acceptable carrier.

The methods of treatment of this disclosure are advantageous in treating diseases where the ELR-CXC chemokine binds to CXCR2. Another embodiment of the disclosure is directed to a method of treating CXCR1/2 chemokine mediated diseases in a patient in need of such treatment comprising administering to the patient a therapeutically effective amount of compound SX-682, or a pharmaceutically acceptable salt or solvate thereof.

Another embodiment of the disclosure is a method of treating CXCR1/2 chemokine mediated diseases in a patient in need thereof comprising administering to the patient (a) an effective amount of the compound having the formula SX-682, or a pharmaceutically acceptable salt or solvate thereof, concurrently or sequentially with (b) at least one additional agent, drug, medicament, antibody and/or inhibitor useful for the treatment of CXCR1/2 chemokine mediated diseases. Examples of the additional medicament, drug or agent include, but are not limited to, disease modifying antirheumatic drugs; nonsteroidal antiinflammatory drugs (NSAIDs); COX-2 selective inhibitors; COX-1 inhibitors; immunosuppressives; steroids; biological response modifiers; and other anti-inflammatory agents or therapeutics useful for the treatment of CXCR1/2 chemokine mediated diseases.

Another embodiment of the method of treating a CXCR1/2 chemokine mediated disease is administering (a) a therapeutically effective amount of the compound having the formula SX-682, or a pharmaceutically acceptable salt or solvate thereof, concurrently or sequentially with (b) at least one medicament selected from the group consisting of: disease modifying antirheumatic drugs; nonsteroidal anti-inflammatory drugs; COX-2 selective inhibitors; COX-1 inhibitors; immunosuppressives; steroids; biological response modifiers; and other anti-inflammatory agents or therapeutics useful for the treatment of CXCR1 and/or CXCR2 chemokine mediated diseases.

Another embodiment of this disclosure is a method for treating cancer in a patient in need of such treatment, the method comprises administering to said patient a therapeutically effective amount of the compound having the formula SX-682, or a pharmaceutically acceptable salt or solvate thereof. Another embodiment of this disclosure is a method for treating cancer comprising administering to the patient a therapeutic amount of the compound having the formula SX-682, or a pharmaceutically acceptable salt or solvate thereof, concurrently or sequentially with (a) at least one antineoplastic agent selected from the group consisting of: (1) gemcitabine, (2) paclitaxel, (3) 5-fluorouracil (5-FU), (4) cyclo-phosphamide, (5) temozolomide and (6) vincristine or (b) at least one agent selected from the group consisting of (1) microtubule affecting agents, (2) antineoplastic agents, (3) anti-angiogenesis agents, (4) VEGF receptor kinase inhibitors, (5) antibodies against the VEGF receptor, (6) interferon, and (7) radiation.

Another embodiment of this disclosure is a method for treating asthma in a patient in need of such treatment the method comprising administering to the patient a therapeutically effective amount of the compound having the formula SX-682, or a pharmaceutically acceptable salt or solvate thereof. Another embodiment of this disclosure is a method for treating a pulmonary disease (e.g., COPD, asthma, or cystic fibrosis), in a patient in need of such treatment, the method comprising administering to the patient a therapeutically effective amount of: (a) the compound having the formula SX-682, or a pharmaceutically acceptable salt or solvate thereof, concurrently or sequentially with (b) at least one compound selected from the group consisting of: glucocorticoids, 5-lipoxygenase inhibitors, beta-2 adrenoceptor agonists, muscarinic M1 antagonists, muscarinic M3 antagonists, muscarinic M2 agonists, NK3 antagonists, LTB4 antagonists, cysteinyl leukotriene antagonists, bronchodilators, PDE4 inhibitors, PDE inhibitors, elastase inhibitors, MMP inhibitors, phospholipase A2 inhibitors, phospholipase D inhibitors, histamine H1 antagonists, histamine H3 antagonists, dopamine agonists, adenosine A2 agonists, NK1 and NK2 antagonists, GABA-β agonists, nociceptin agonists, expectorants, mucolytic agents, decongestants, antioxidants, anti-IL-8 antibodies, anti-IL-5 antibodies, anti-IgE antibodies, anti-TNF antibodies, IL-10, adhesion molecule inhibitors, and growth hormones.

Another embodiment of this disclosure is a method for treating multiple sclerosis, comprising administering to the patient: (a) a therapeutically effective amount of the compound having the formula SX-682, or a pharmaceutically acceptable salt or solvate thereof, concurrently or sequentially with (b) a therapeutically effective amount of at least one compound selected from the group consisting of: glatiramer acetate, glucocorticoids, methotrexate, azothioprine, mitoxantrone, and CB2-selective inhibitors.

Another embodiment of this disclosure is a method of treating multiple sclerosis comprising concurrent or sequential administration of a therapeutically effective amount of: (a) the compound having the formula SX-682, or a pharmaceutically acceptable salt or solvate thereof, and (b) at least one compound selected from the group consisting of: methotrexate, cyclosporin, leflunimide, sulfasalazine, β-methasone, β-interferon, glatiramer acetate, prednisone, etonercept, and infliximab.

Another embodiment of this disclosure is a method for treating rheumatoid arthritis in a patient in need of such treatment comprising administering to said patient a therapeutically effective amount of the compound having the formula SX-682, or a pharmaceutically acceptable salt or solvate thereof.

Another embodiment of this disclosure is a method for treating rheumatoid arthritis in a patient in need of such treatment comprising administering to said patient a therapeutically effective amount of the compound having the formula SX-682, or a pharmaceutically acceptable salt or solvate thereof, in combination with at least one compound selected from the group consisting of COX-2 inhibitors, COX-1 inhibitors, immunosuppressives (e.g., methotrexate, aminopterin, cyclosporin, leflunimide and sulfasalazine), steroids (e.g., betamethasone, cortisone and dexamethasone), PDE 4 inhibitors, anti-TNF-alpha compounds, MMP inhibitors, glucocorticoids, chemokine inhibitors, CB2-selective agents, and other classes of compounds indicated for the treatment of rheumatoid arthritis.

Another embodiment of this disclosure is a method for treating stroke and ischemia reperfusion injury in a patient in need of such treatment the method comprising administering to the patient a therapeutically effective amount of: (a) the compound having the formula SX-682, or a pharmaceutically acceptable salt or solvate thereof, concurrently or sequentially with (b) at least one compound selected from the group consisting of: thrombolitics (e.g., tenecteplase, TPA, alteplase), antiplatelet agents (e.g., gpIIb/IIIa), antagonists (e.g., abciximab and eftiifbatide), anticoagulants (e.g., heparin), and other compounds indicated for the treatment of stroke and ischemia reperfusion injury.

Another embodiment of this disclosure is a method for treating stroke and ischemia reperfusion injury in a patient in need of such treatment the method comprising administering to the patient a therapeutically effective amount of: (a) the compound having the formula SX-682, or a pharmaceutically acceptable salt or solvate thereof concurrently or sequentially with (b) at least one compound selected from the group consisting of: tenecteplase, TPA, alteplase, abciximab, eftiifbatide, and heparin.

Another embodiment of this disclosure is a method for treating psoriasis in a patient in need of such treatment, the method comprising administering to the patient a therapeutically effective amount of: a) the compound having the formula SX-682, or a pharmaceutically acceptable salt or solvate thereof, concurrently or sequentially with (b) at least one compound selected from the group consisting of: immunosuppressives (e.g., methotrexate, aminopterin, cyclosporin, efalizumab, alefacept, leflunimide and sulfasalazine), steroids (e.g., β-methasone) and anti-TNFα compounds (e.g., etonercept and infliximab).

This disclosure also provides a method for treating CXCR1/2 mediated disease or condition selected from the group consisting of: pain (e.g., acute pain, acute inflammatory pain, chronic inflammatory pain, and neuropathic pain), acute inflammation, chronic inflammation, rheumatoid arthritis, psoriasis, atopic dermatitis, asthma, bronchopulmonary dysplasia, COPD, adult respiratory disease, arthritis, inflammatory bowel disease, Crohn's disease, ulcerative colitis, septic shock, endotoxic shock, gram negative sepsis, toxic shock syndrome, stroke, ischemia reperfusion injury, renal reperfusion injury, glomerulonephritis, thrombosis, Alzheimer's disease, graft vs. host reaction (i.e., graft-versus-host disease), allograft rejections (e.g., acute allograft rejection, and chronic allograft rejection), malaria, acute respiratory distress syndrome, delayed type hypersensitivity reaction, atherosclerosis, cerebral ischemia, cardiac ischemia, osteoarthritis, multiple sclerosis, restinosis, angiogenesis, angiogenesis associated with tumor growth, osteoporosis, gingivitis, respiratory viruses, herpes viruses, hepatitis viruses, HIV, Kaposi's sarcoma associated virus (i.e., Kaposi's sarcoma), meningitis, cystic fibrosis, pre-term labor, cough, pruritus, multi-organ dysfunction, trauma, strains, sprains, contusions, psoriatic arthritis, herpes, encephalitis, CNS vasculitis, traumatic brain injury, systemic tumors, CNS tumors, tumors dependent on angiogenesis for growth, leukopenia and neutropenia, chemotherapy-induced leukopenia and neutropenia, opportunistic infections associated with neutropenia or leukopenia, subarachnoid hemorrhage, post surgical trauma, interstitial pneumonitis, hypersensitivity, crystal induced arthritis, acute pancreatitis, chronic pancreatitis, acute alcoholic hepatitis, necrotizing enterocolitis, chronic sinusitis, angiogenic ocular disease, ocular inflammation, retinopathy of prematurity, diabetic retinopathy, macular degeneration with the wet type preferred, corneal neovascularization, polymyositis, vasculitis, acne, gastric ulcers, duodenal ulcers, celiac disease, esophagitis, glossitis, airflow obstruction, airway hyperresponsiveness (i.e., airway hyperreactivity), bronchiectasis, bronchiolitis, bronchiolitis obliterans, chronic bronchitis, cor pulmonae, dyspnea, emphysema, hypercapnea, hyperinflation, hypoxemia, hyperoxia-induced inflammations, hypoxia, surgical lung volume reduction, pulmonary fibrosis, pulmonary hypertension, right ventricular hypertrophy, peritonitis associated with continuous ambulatory peritoneal dialysis (CAPD), granulocytic ehrlichiosis, sarcoidosis, small airway disease, ventilation-perfusion mismatching, wheeze, colds, gout, alcoholic liver disease, lupus, burn therapy (i.e., the treatment of burns), periodontitis, cancer, transplant reperfusion injury, early transplantation rejection (e.g., acute allograft rejection) in a patient in need of such treatment comprising administering to said patient an effective amount of the compound having the formula SX-682, or a pharmaceutically acceptable salt or solvate thereof.

Another embodiment of this disclosure is a method for treating diseases such as allograft rejections, early transplantation rejections, autoimmune deafness, myocarditis, neuropathies, autoimmune diseases and vasculitis syndromes wherein said:
  (a) allograft rejections are selected from the group consisting of acute allograft rejections and chronic allograft rejections;
  (b) early transplantation rejection is an acute allograft rejection; (c) autoimmune deafness is Meniere's disease;
  (d) myocarditis is viral myocarditis;
  (e) neuropathies are selected from the group consisting of IgA neuropathy, membranous neuropathy and idiopathic neuropathy;
  (f) autoimmune diseases are anemias; and (g) vasculitis syndromes are selected from the group consisting of giant cell arteries, Behcet's disease and Wegener's granulomatosis.

Another embodiment of this disclosure is a method for treating COPD in a patient in need of such treatment comprising administering to said patient a therapeutically effective amount of the compound having the formula SX-682, or a pharmaceutically acceptable salt or solvate thereof.

Another embodiment of this disclosure is a method for treating arthritis in a patient in need of such treatment comprising administering to said patient a therapeutically effective amount of the compound having the formula SX-682, or a pharmaceutically acceptable salt or solvate thereof.

Another embodiment of this disclosure is a method for treating osteoarthritis in a patient in need of such treatment comprising administering to said patient a therapeutically effective amount of the compound having the formula SX-682, or a pharmaceutically acceptable salt or solvate thereof.

Another embodiment of this disclosure is a method for treating pain in a patient in need of such treatment comprising administering to said patient a therapeutically effective amount of the compound having the formula SX-682, or a pharmaceutically acceptable salt or solvate thereof.

Another embodiment of this disclosure is a method for treating pain in a patient in need of such treatment comprising administering to said patient a therapeutically effective amount of the compound having the formula SX-682, or a pharmaceutically acceptable salt or solvate thereof, and administering a therapeutically effective amount of at least one medicament selected from the group consisting of: NSAIDs, COXIB inhibitors (e.g., COX-1 and COX-2 inhibitors), anti-depressants, and anti-convulsants.

Another embodiment of this disclosure is a method for treating acute pain in a patient in need of such treatment comprising administering to said patient a therapeutically effective amount of the compound having the formula SX-682, or a pharmaceutically acceptable salt or solvate thereof.

Another embodiment of this disclosure is a method for treating acute inflammatory pain in a patient in need of such treatment comprising administering to said patient a therapeutically effective amount of the compound having the formula SX-682, or a pharmaceutically acceptable salt or solvate thereof.

Another embodiment of this disclosure is a method for treating chronic inflammatory pain in a patient in need of such treatment comprising administering to said-patient a therapeutically effective amount of the compound having the formula SX-682, or a pharmaceutically acceptable salt or solvate thereof.

Another embodiment of this disclosure is a method for treating neuropathic pain in a patient in need of such treatment comprising administering to said patient a therapeutically effective amount of the compound having the formula SX-682, or a pharmaceutically acceptable salt or solvate thereof.

Another embodiment of this disclosure is a pharmaceutical composition comprising the compound having the formula SX-682, or a pharmaceutically acceptable salt or solvate thereof, and at least one other agent, medicament, antibody and/or inhibitor disclosed above, and a pharmaceutically acceptable carrier.

In general the compounds used to treat pain will have CXCR1/2 antagonistic activity.

NSAIDs are well known to those skilled in the art and can be used in their known dosages and dosage regimens. Examples of NSAIDs include but are not limited to: piroxicam, ketoprofen, naproxen, indomethacin, and ibuprofen COXIB inhibitors are well known to those skilled in the art and can be used in their known dosages and dosage regimens. Examples of COXIB inhibitors include, but are not limited to: rofecoxib and celecoxib. Anti-depressants are well known to those skilled in the art and can be used in their known dosages and dosage regimens. Examples of anti-depressants include but are not limited to: amitriptyline and nortriptyline. Anti-convulsants are well known to those skilled in the art and can be used in their known dosages and dosage regimens. Examples of anti-convulsants include but are not limited to: gabapentin, carbamazepine, pregabalin, and lamotragine.

Pharmaceutical Compositions

For preparing pharmaceutical compositions from the compound of formula SX-682, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, microcrystalline cellulose, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington: The Science and Practice of Pharmacy*, 20th Edition, (2000), Lippincott Williams & Wilkins, Baltimore, Md. which is incorporated herein by reference.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration. Liquid form preparations may also include dissolution in lipid-based, self-emulsifying drug delivery systems (SEDDS) such as LABRASOL® or GELUCIRE® for oral administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compound of formula SX-682 may also be deliverable transdermally. The transdermal composition can take the form of creams, lotions, aerosols and/or emulsions and can be included in a transdermal patch of the matrix or reservoir type as are conventional in the art for this purpose.

The compound of formula SX-682 can be administered orally.

A suitable pharmaceutical preparation is in a unit dosage form. In such form, the preparation is subdivided into suitably sized unit doses containing appropriate quantities of the active component, e.g., an effective amount to achieve the desired purpose.

The quantity of active compound of formula SX-682 in a unit dose of preparation may be varied or adjusted from about 0.01 mg to about 1000 mg, or from about 0.01 mg to about 750 mg, or from about 0.01 mg to about 500 mg, or from about 0.01 mg to about 250 mg, according to the particular application.

The actual dosage employed may be varied depending upon the requirements of the patient and the severity of the condition being treated. Determination of the proper dosage regimen for a particular situation is within the skill of the art. For convenience, the total dosage may be divided and administered in portions during the day as required.

The amount and frequency of administration of the compound of formula SX-682 and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 0.04 mg/day to about 4000 mg/day, in two to four divided doses, or given preferably as a single once-daily dose. Once-weekly and twice-weekly dosing is also preferable.

The amount and frequency of administration of the compound of formula SX-682 and the chemotherapeutic agents and/or radiation therapy will be regulated according to the judgment of the attending clinician (physician) considering such factors as age, condition and size of the patient as well as severity of the disease being treated. A dosage regimen of the compound having the formula SX-682 can be orally administration of from 10 mg to 2000 mg/day, or 10 to 1000 mg/day, or 50 to 600 mg/day, in two to four (or two) divided doses, to block tumor growth. Intermittent therapy (e.g., one week out of three weeks or three out of four weeks) may also be used.

The chemotherapeutic agent and/or radiation therapy can be administered according to therapeutic protocols well known in the art. It will be apparent to those skilled in the art that the administration of the chemotherapeutic agent and/or radiation therapy can be varied depending on the disease being treated and the known effects of the chemotherapeutic agent and/or radiation therapy on that disease. Also, in accordance with the knowledge of the skilled clinician, the therapeutic protocols (e.g., dosage amounts and times of administration) can be varied in view of the observed effects of the administered therapeutic agents (i.e., antineoplastic agent or radiation) on the patient, and in view of the observed responses of the disease to the administered therapeutic agents.

If the compound of formula SX-682, and the chemotherapeutic agent and/or radiation is not administered simultaneously or essentially simultaneously, then the initial order of administration of the compound of formula SX-682, and the chemotherapeutic agent and/or radiation, may not be important. Thus, the compound of formula SX-682 may be administered first, followed by the administration of the chemotherapeutic agent and/or radiation; or the chemotherapeutic agent and/or radiation may be administered first, followed by the administration of the compound of formula SX-682. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the patient.

For example, the chemotherapeutic agent and/or radiation may be administered first, especially if it is a cytotoxic agent, and then the treatment continued with the administration of the compound having the formula SX-682 followed, where determined advantageous, by the administration of the chemotherapeutic agent and/or radiation, and so on until the treatment protocol is complete.

The particular choice of the compound of formula SX-682, and chemotherapeutic agent and/or radiation will depend upon the diagnosis of the attending physicians and their judgment of the condition of the patient and the appropriate treatment protocol.

Also, in general, the compound of formula SX-682 and the chemotherapeutic agent do not have to be administered in the same pharmaceutical composition, and may, because of different physical and chemical characteristics, have to be administered by different routes. For example, the compound of formula SX-682 may be administered orally to generate and maintain good blood levels thereof, while the chemotherapeutic agent may be administered intravenously. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

Thus, in accordance with experience and knowledge, the practicing physician can modify each protocol for the administration of a component (therapeutic agent; i.e., the compound of formula SX-682, chemotherapeutic agent or radiation) of the treatment according to the individual patient's needs, as the treatment proceeds.

The attending clinician, in judging whether treatment is effective at the dosage administered, will consider the general well-being of the patient as well as more definite signs such as relief of disease-related symptoms, inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

The disclosure provided herein is exemplified by the following preparations and examples that should not be construed to limit the scope of the disclosure. Alternative mechanistic pathways and analogous structures may be apparent to those skilled in the art.

Synthesis Example 1: Synthesis of
N-(4-fluorophenyl)-2-chloro-pyrimidinamide

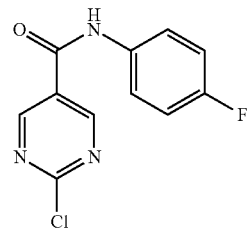

3

2-Chloro-pyrimidine-5-carboxylic acid (3.16 g, 20 mmol) was suspended in dichloromethane (40 mL), and oxalyl chloride (3.30 g, 26 mmol) was added, followed by dimethylformamide as catalyst. The reaction started to vigorously evolve gas. The reaction was heated to reflux for 1 hour, then allowed to cool to room temperature. 4-Fluoroaniline was added, vigorous bubbling was seen again, and the reaction mixture warmed up considerably. Triethylamine was added, and a flocculent precipitate immediately formed. The reaction mixture was heated to reflux once again for another hour, removed from heat, and stirred at room temperature for 18 hours under nitrogen. The reaction was diluted with ethyl acetate (100 mL), and the organic layer washed with water, saturated sodium bicarbonate, water, 1N HCl, water, saturated sodium chloride, then dried over sodium sulfate. The liquid was filtered, and evaporated to yield 3.44 g (68%) of compound 3 as a light yellow solid. ESI-MS m/z=252.0 [M+H]$^+$.

Synthesis Example 2: Synthesis of
2-Mercapto-pyrimidine-5-carboxylic acid
(4-fluoro-phenyl)-amide Intermediate 4

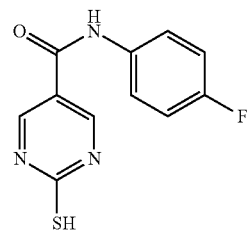 [SMILES: O=C(Nc1ccc(F)cc1)c1cnc(S)nc1]

In a round bottom flask, 2-chloro-pyrimidine-5-carboxylic acid (4-fluoro-phenyl)-amide 3 (2.52 g, 10.0 mmol) and anhydrous sodium hydrogen sulfide (1.22 g, 21.8 mmol) were suspended in anhydrous dimethylformamide (20 mL).

The suspension was stirred at room temperature, and the reaction mixture turned a deep green color. After 1 h, the reaction mixture was partioned between ethyl acetate and water, and transferred to a separatory funnel. After the layers were separated, the ethyl acetate layer was washed twice with a 2:1 mixture of water and 5% sodium bicarbonate. The combined aqueous layers were acidified with 1 N HCl precipitating a yellow solid. The suspension was left to stand at room temperature for 2 hours, then the precipitate was collected by vacuum filtration, rinsing with water. The yellow solid was dried overnight in a vacuum desiccator to yield 2.3 g (92%) of the thiopyrimidinamide intermediate 4. ESI-MS m/z=250.0 [M+H]$^+$. $^1$H NMR (300 MHz, DMSO-d$_6$) δ 10.29 (s, 1H), 8.77 (bs, 2H), 7.77-7.70 (m, 2H), 7.24 (t, J=8.9 Hz, 2H).

Synthesis Example 3: Synthesis of Pinacol Ester Derivative 5

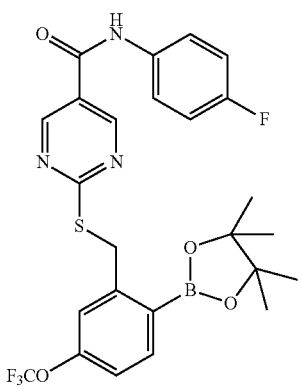 [SMILES: CC1(C)OB(c2ccc(OC(F)(F)F)cc2CSc2ncc(C(=O)Nc3ccc(F)cc3)cn2)OC1(C)C]

2-Mercapto-pyrimidine-5-carboxylic acid (4-fluoro-phenyl)-amide intermediate 4 (2.32 g, 9.3 mmol) and 2-bromomethyl-4-trifluoromethoxy-phenylboronic acid, pinacol ester (3.85 g, 10.1 mmol) were suspended in anhydrous DMF (20 ml). Sonication was used to dissolve the compounds. To the reaction flask triethylamine (2.8 mL, 20.1 mmol) was added and a precipitate (triethylamine-HBr) formed immediately. The reaction was layered with nitrogen gas and left to stand at room temperature for 3.75 hr. The reaction was poured into water (500 mL) and layered with ethyl acetate. The biphasic solution was transferred to a separatory funnel and diluted further with ethyl acetate and brine. The layers were separated, and the aqueous layer was extracted twice more with ethyl acetate. The combined ethyl acetate layers were dried over sodium sulfate, gravity filtered, and dried in vacu to yield 5.7 g (>100%, 93% pure by LC-MS) of a red oil, 2-[2-(4,4,5,5-tetramethyl-[1,3,2]dioxaborolan-2-yl)-5-trifluoromethoxy-benzylsulfanyl]-pyrimidine-5-carboxylic acid (4-fluoro-phenyl)-amide 6. ESI-MS m/z=550.1 [M+H]$^+$. $^1$H NMR (500 MHz, DMSO-d$_6$) δ 10.52 (s, 1H), 9.11 (s, 2H), 7.81 (d, J=8.2 Hz, 1H), 7.78-7.75 (m, 2H), 7.55 (s, 1H), 7.28-7.22 (m, 3H), 4.72 (s, 2H), 1.32 (s, 12H). The NMR spectrum also contained peaks consistent with the presence of residual DMF. The product was carried forward without further purification.

Synthesis Example 4: Synthesis of Compound SX-682

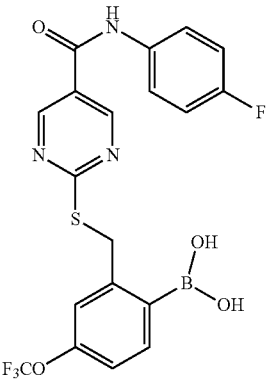 [SMILES: O=C(Nc1ccc(F)cc1)c1cnc(SCc2cc(OC(F)(F)F)ccc2B(O)O)nc1]

SX-682 was obtained by deprotection of the boronic acid pinacol ester. Compound 6 (5.66 g, 10.3 mmol, 1 eq.) was dissolved in methanol (100 mL). The reaction vessel was charged with 4.5 M aqueous potassium hydrogen fluoride (11.5 mL, 5 eq.) and the resulting orange solution was stirred for 1 hour. The methanol was removed by rotary evaporation at room temperature and the resulting mixture of yellow and off-white solids was suspended in acetone. The suspension was gravity filtered to remove the insoluble salts, and the resulting clear yellow solution was added via pipette to a flask of water (2 L) and placed in the refrigerator. After cooling for about 1.5 hours, the resulting off-white precipitate was collected by vacuum filtration, rinsing with water. The funnel was dried overnight in a vacuum desiccator to afford 3.87 g (80% yield, >99% purity by LC-MS) of 2-(2-boronic acid-5-trifluoromethoxy-benzylsulfanyl)-pyrimidine-5-carboxylic acid (4-fluoro-phenyl)-amide. ESI-MS m/z=468.1 [M+H]$^+$. $^1$H NMR (300 MHz, DMSO-d6) δ 10.49 (s, 1H), 9.09 (s, 2H), 8.33 (bs, 2H), 7.78-7.73 (m, 2H), 7.66 (d, J=8.5 Hz, 1H), 7.46 (s, 1H), 7.25-7.19 (m, 3H), 4.70 (s, 2H).

Pharmacology Example 1: In Vitro Inhibition of Intracellular Calcium Release by SX-682

An in vitro assay showed inhibition of CXCR1/2-mediated intracellular calcium release by SX-682. Briefly, cells (either isolated human neutrophils or RBL cells stably transfected with either CXCR1 or CXCR2) were suspended in HBSS$^-$ (without Ca$^{2+}$ and Mg$^{2+}$) containing 10 mM HEPES and FLIPR calcium 3 dye (3.1×10$^7$ cells in total volume 1.7 mL). Cells were aliquoted (200 µL of the cell suspension per tube, 8 tubes total) and 2 µL of the designated compound (with appropriate dilutions) were added to each of 6 tubes. As controls, 2 µL of DMSO (1% final concentration) were added to 2 other tubes. Cells were incubated for 30 min at 37° C. After dye loading, tubes were centrifuged at 6,000 rpm for 1 min, supernatant was removed and the cell pellet was re-suspended in 200 µL of HBSS$^+$ (with Ca$^{2+}$ and Mg$^{2+}$) containing 10 mM HEPES. The test compound or DMSO (control) was added again at the same concentrations that were used during cell loading. The cell suspension was aliquoted into a 96-well reading plate (Corning) in a volume of 90 µL (10$^5$ cells/well). The compound plate contained agonist (CXCL8 in HBSS$^-$) or HBSS$^-$ (control). After 15 sec of reading the basal level of fluorescence by FlexStation II, 10 µL of CXCL8 or HBSS⁻ were automatically transferred from the compound plate into the reading plate (final concentration of CXCL8 was 25 nM). Changes in fluorescence were monitored (ex=485 nm, em=525 nm) every 5 s for 240 to 500 s at room temperature.

The maximum change in fluorescence, expressed in arbitrary units over baseline (Max-Min), was used to determine the CXCL8 response. The effect of each compound on the CXCL8 response was normalized and expressed as a percent of the DMSO control, which was designated as "100% response." Curve fitting and calculation of the compound inhibitory concentration that reduces the level of the CXCL8 response by 50% ($IC_{50}$), or the compound agonist concentration that increases the level of the calcium release by 50% of the maximum agonist-induced change ($EC_{50}$) were determined by nonlinear regression analysis of the dose-response curves generated using Prism 4 (GraphPad Software, Inc., San Diego, Calif.).

The mean (±SE) $IC_{50}$ for SX-682 (n=4) was 42±3 nM, 20±2 nM and 55±6 nM in CXCR1 transfected RBL cells ('CXCR1', squares), CXCR2 transfected RBL cells ('CXCR2', inverted triangles), and human neutrophils ('Human PMNs', circles), respectively (FIG. 1).

Pharmacology Example 2: SX-682 Exhibits Sustained Wash-Resistant Inhibition of Intracellular Calcium Release SX-682 contains a boronic acid moiety that has the potential to form a transient covalent linkage with hydroxyl-bearing amino acid side chains in the binding site of its protein target. Without wishing to be bound by theory, we hypothesized that such a transient covalent linkage in the binding site of SX-682 might result in CXCR1/2 inhibition that was sustained after inhibitor washout. If inhibition is sustained in vitro after SX-682 washout, inhibition may also be sustained in vivo after SX-682 has been eliminated from the plasma, a property that would permit infrequent patient dosing regimens (e.g. once-daily, twice-weekly and once-weekly). Infrequent dosing regimens are preferred embodiments.

In order to test this hypothesis, RBL cells ($10^7$ cells/mL) stably transfected with either CXCR1 or CXCR2 were (1) incubated with SX-682 at various concentrations for 30 minutes at 37° C., (2) washed and resuspended in assay buffer (RPMI/2% serum) at room temperature, and (3) assayed for CXCL8-mediated calcium response at time points up to 12 h after inhibitor washout. The concentrations of SX-682 tested were 0 (positive control), 0 (negative control), 0.4, 2, and 10 µM. At 30 minutes before each time point, a 56.25 µL aliquot of the cells were removed and loaded for 30 minutes at room temperature in the dark with FLIPR-3 reagent (262.5 µL per tube). Following FLIPR-3 incubation, cells were assayed for CXCL8 mediated intracellular calcium release as described in Pharmacology Example 1.

Figure 2:
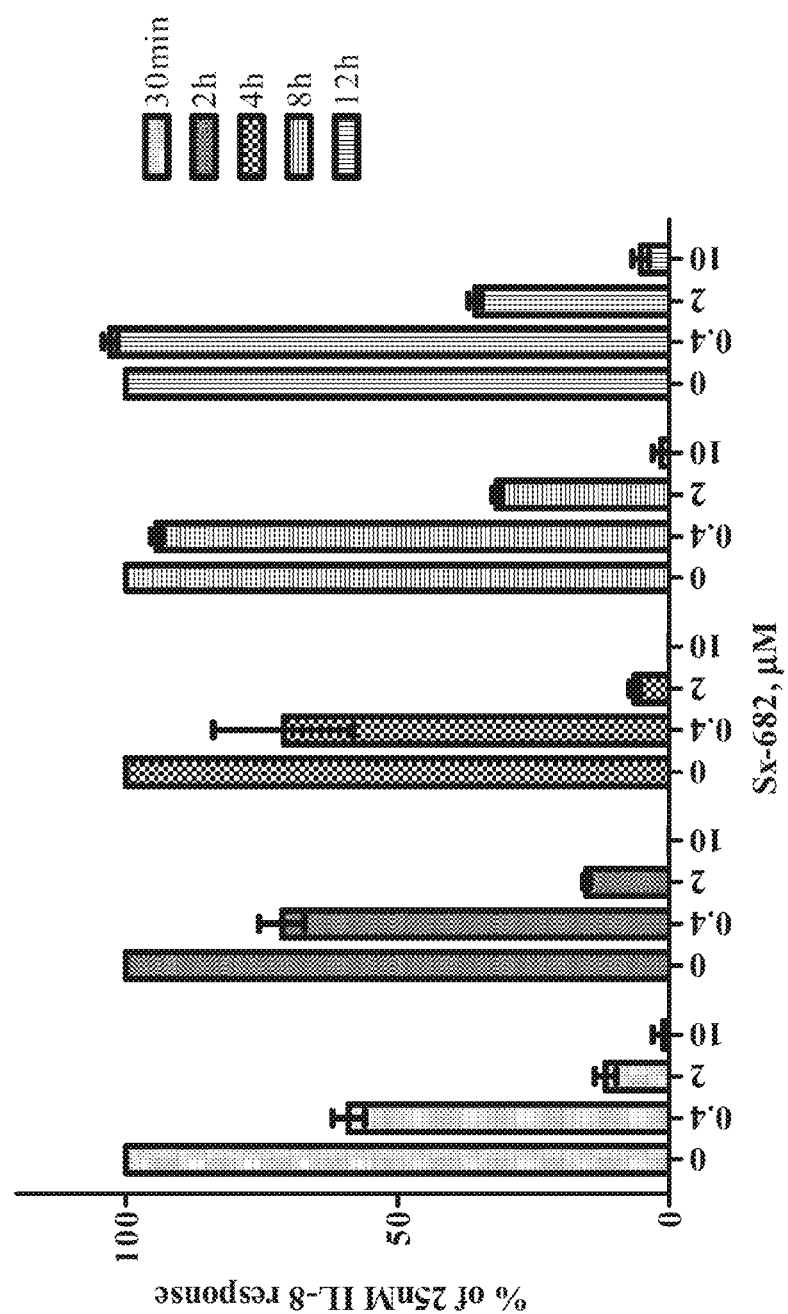
FIG. 2 shows that inhibition of CXCL8-mediated intracellular calcium flux in RBL cells stably transfected with CXCR1 is sustained for at least 12 hours after SX-682 washout.
Figure 3:
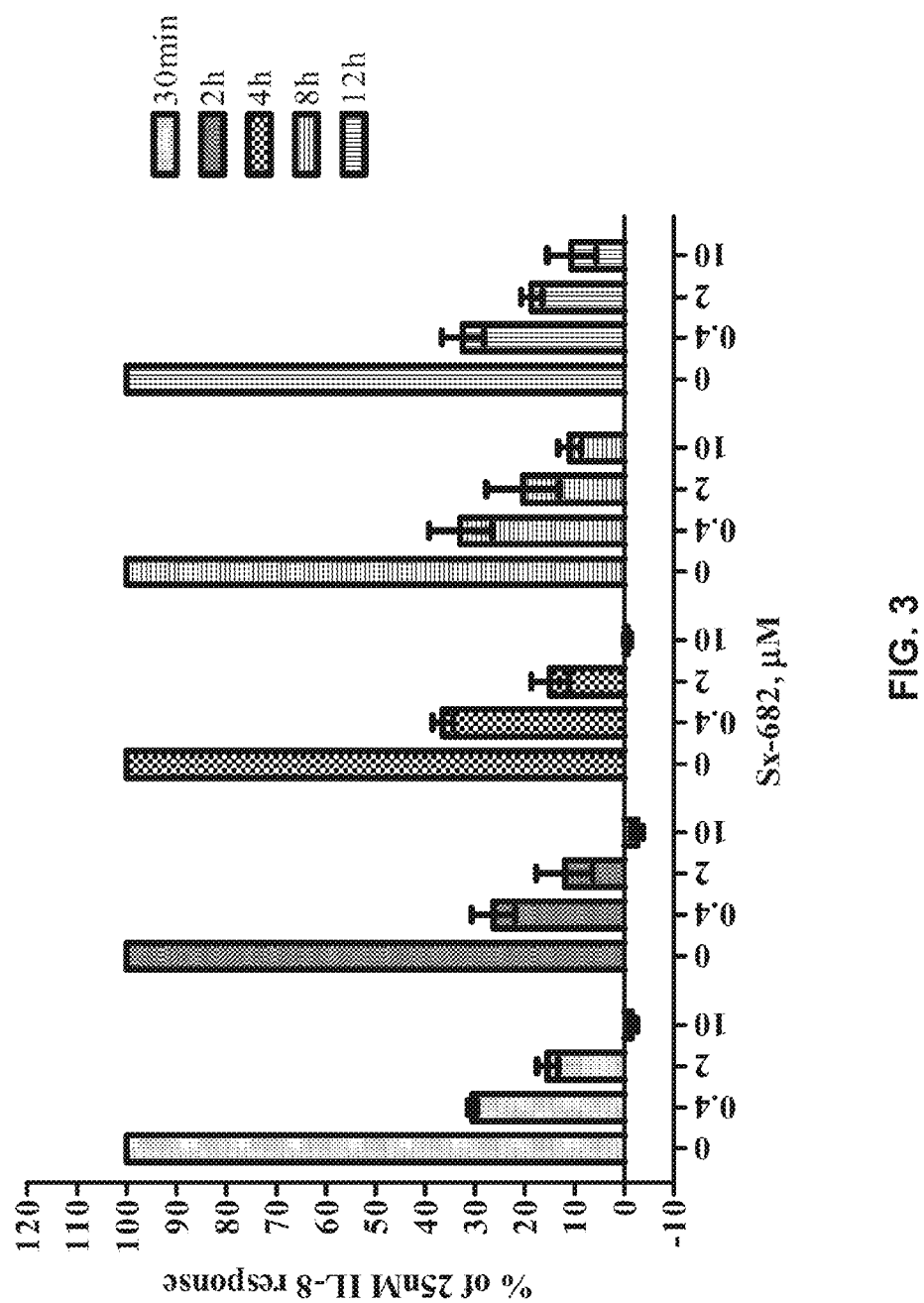
FIG. 3 shows that inhibition of CXCL8-mediated intracellular calcium flux in RBL cells stably transfected with CXCR2 is sustained for at least 12 hours after SX-682 washout.

Consistent with our hypothesis, SX-628 exhibited inhibition of CXCL8-mediated intracellular calcium flux in RBL cells stably transfected with either CXCR1 (FIG. 2) or CXCR2 (FIG. 3) that was sustained for at least 12 hours after SX-682 washout.

Figure 4:
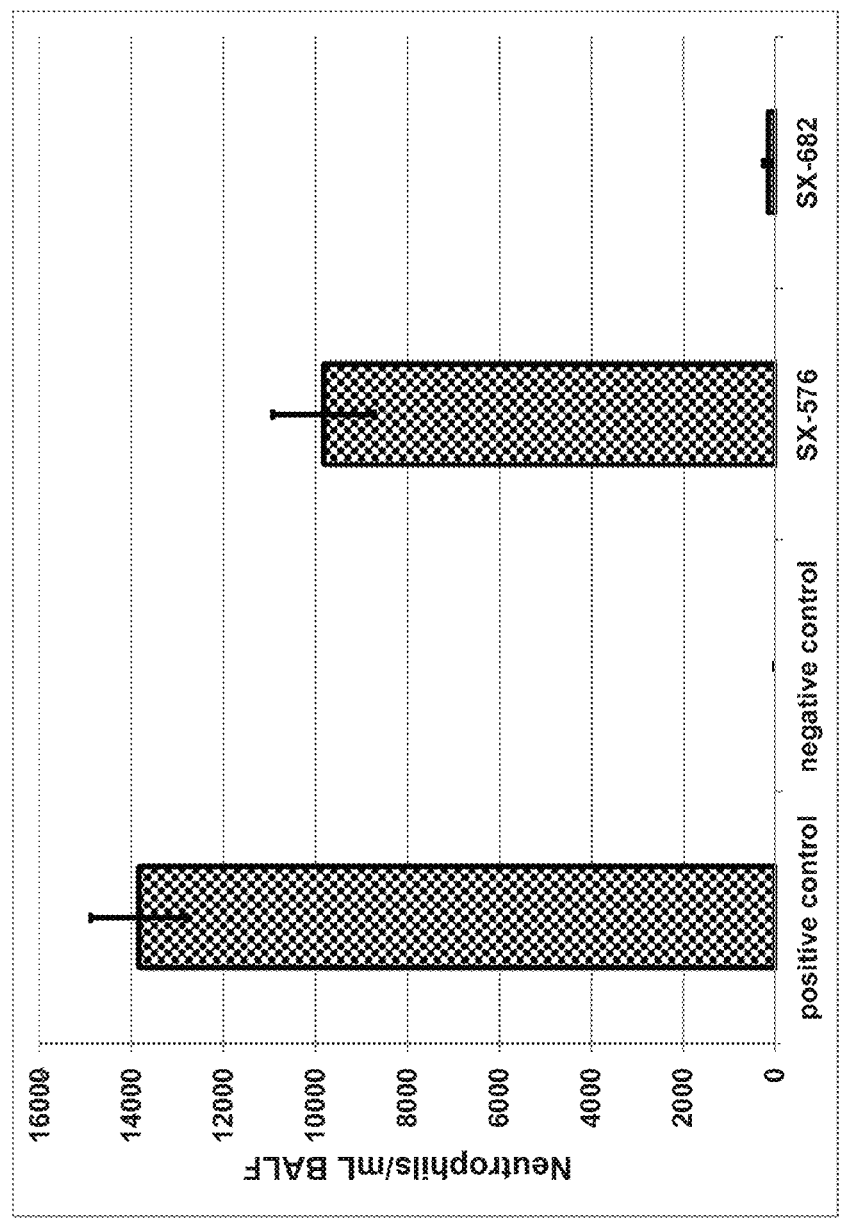
FIG. 4 shows the effect of intravenous dosing of either SX-576 or SX-682 on neutrophil influx in the ozone rat model of pulmonary inflammation.

Pharmacology Example 3: SX-682 Exhibits Pronounced Activity in the Rat Model of Pulmonary Inflammation SX-682 was assayed in an in vivo rat model of pulmonary inflammation. Activity in this model of pulmonary inflammation provides evidence that supports the use of SX-682 in the treatment of a number of pulmonary inflammatory diseases, including chronic obstructive pulmonary disease (COPD) and bronchopulmonary dysplasia (BPD). In this experiment, Sprague-Dawley rats (n=4 per cohort) were dosed intravenously only once at t=0 with either vehicle control (dimethylformamide/PEG400/saline, 40:40:20), positive inhibitor control (SX-576, 1 mg/kg) or the test compound (SX-682, 1 mg/kg). The rats were then placed in air (negative exposure group; vehicle control only) or 1 ppm ozone (positive exposure group; vehicle control, positive inhibitor control SX-576, and test compound SX-682) for 4 hours. The rats were then sacrificed at t=24 hours, and the bronchoalveolar lavage fluid (BALF) was collected. The cells were spun down, stained with Wright-Giemsa and counted. In the negative exposure group, no neutrophils were observed when stained. In the ozone exposed rats treated with vehicle however, there was a brisk influx of neutrophils of approximately 14,000 per mL of BALF (FIG. 4). In contrast, both SX-576 and SX-682 (each at 1 mg/kg) significantly decreased the influx of neutrophils into the lungs as compared to control rats treated with vehicle only (FIG. 4). Of the two inhibitors tested, SX-682 exhibited a markedly more robust inhibition of neutrophil chemotaxis (FIG. 4). Notably, the inhibition of neutrophil influx into the BALF was sustained for 24 hours after only a single dose of 1 mg/kg of SX-682. These results provide evidence that SX-682 is a potent inhibitor of pulmonary neutrophil chemotaxis in vivo, and is effective for treating diseases with a heightened pulmonary inflammation component, like COPD in a predictive in vivo model.

Stability Example 1: Increased Microsomal Stability of SX-682

Figure 5:
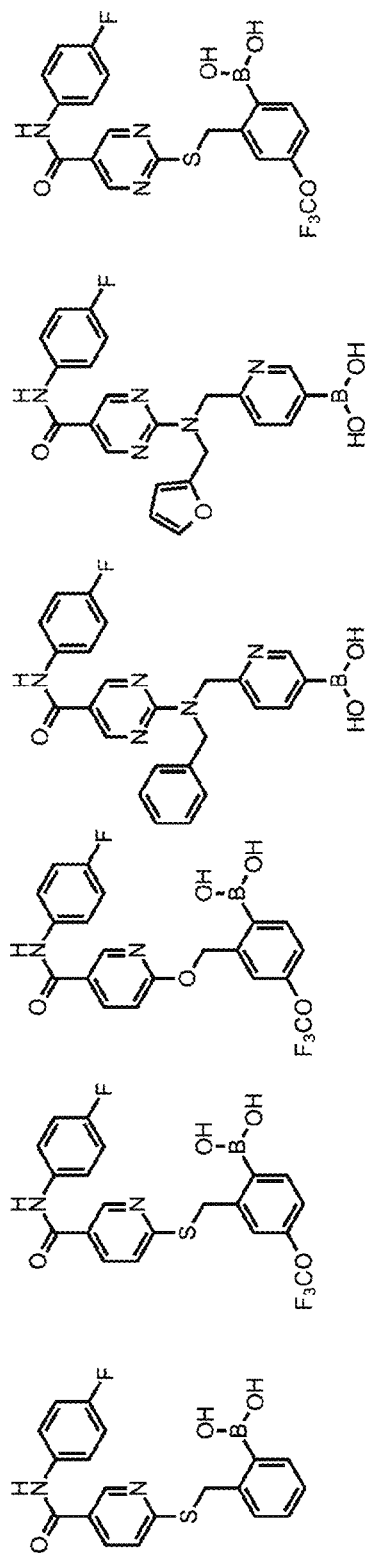
FIG. 5 illustrates boronic acid containing CXCR1/CXCR2 inhibitors.
Figure 6:
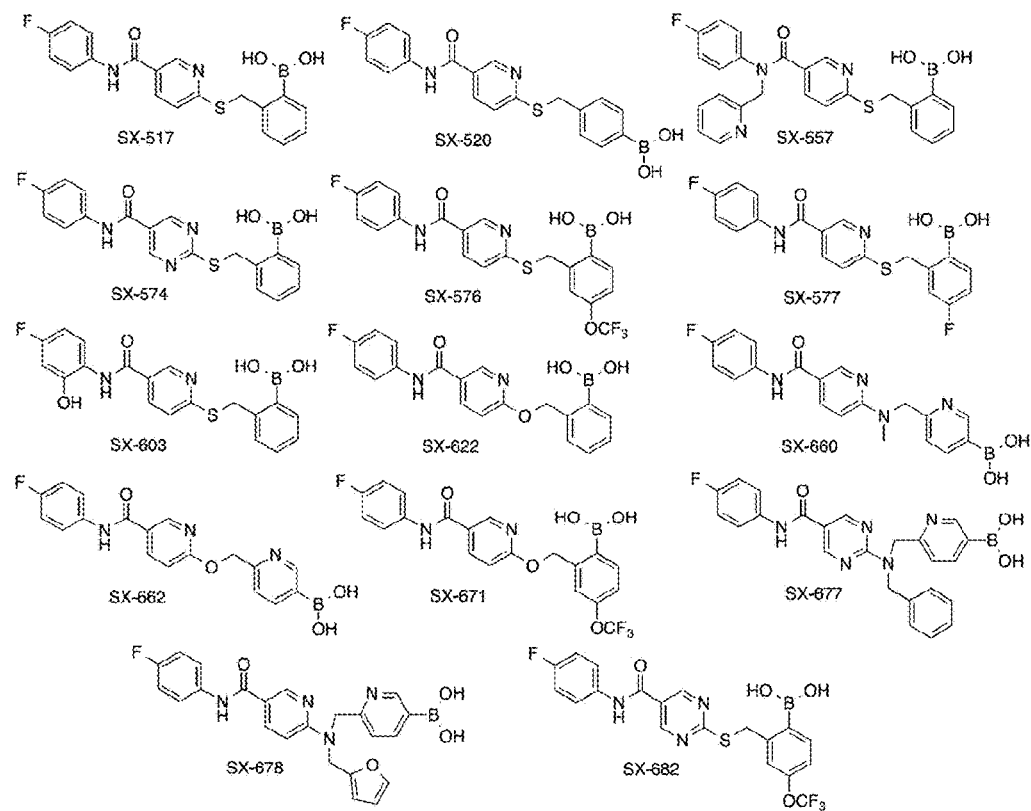
FIG. 6 shows structures of selected antagonists of CXCR1 and/or CXCR2 of formula I that include SX-517, SX-520, SX-557, SX-574, SX-577, SX-603, SX-622, SX-660, SX-662, SX-671, SX-677, SX-678, and SX-682.

Liver microsomes are an in vitro model for in vivo metabolism and elimination of a drug by the liver (and gut) cytochrome P450 system. A compound's stability in liver microsomes in vitro is predictive of its metabolism and elimination in vivo. The stability of SX-682 in liver microsomes together with several other cogeners was examined to quantify the microsomal stability of SX-682 and identify potential structure-activity relationships (SAR) predictive of stability or instability (FIG. 5).

The compounds were incubated in duplicate with human liver microsomes at 37° C. The reaction contained microsomal protein in 100 mM potassium phosphate, 2 mM NADPH, 3 mM $MgCl_2$, pH 7.4. A control was run for each compound omitting NADPH to detect NADPH-independent degradation. An aliquot was removed from each experimental and control reaction at 0, 10, 20, 30, and 60 minutes and mixed with an equal volume of ice-cold Stop Solution (0.3% acetic acid in acetonitrile containing haloperidol, diclofenac, or other internal standard). Stopped reactions were incubated for at least ten minutes at −20° C., and an additional volume of water was added. The samples were centrifuged to remove precipitated protein, and the supernatants were analyzed by LCMS/MS to quantitate the remaining compound. Data were converted to percent remaining by dividing by the time zero concentration value. Data were fit to a first-order decay model to determine half-life. Intrinsic clearance was calculated from the half-life and the protein concentrations:

$CL_{int}=\ln(2)/(t½ \text{ [microsomal protein]}).$

The results are shown in Table 1. Surprisingly, SX-682 was markedly more stable than SX-671 or SX-576 (6-fold larger half-life), even though the latter is structurally identical but for a single ring nitrogen. On the other hand, the introduction of a ring nitrogen was insufficient alone to impart the stability seen with SX-682 as demonstrated by SX-677 and SX-678, which have half-lives that are 2-fold and 5-fold smaller than SX-682, respectively. More surprising is that eliminating the ring nitrogen in SX-517 yielded a half-life even larger than that of SX-682. The results as a whole led to no SAR predictive of the surprising stability of SX-682.

TABLE 1

Stability in human liver microsomes (NADPH-dependent)

| Parameter | SX-517 | SX576 | SX-671 | SX-677 | SX-678 | SX-682 |
|---|---|---|---|---|---|---|
| $CL_{int}^{a}$ (μL/min mg) | 3.4 | 45.7 | 16.2 | 15.9 | 33.4 | 2.1 |
| $t½^{b}$ (min) | 405 | 50 | 143 | 145 | 69.2 | 325 |

[a]microsomal intrinsic clearance
[b]half-life

Metabolic Stability Example 2: Increased Plasma Stability of SX-682

The in vitro stability of SX-682 and the cogeners of Metabolic Stability Example 1 (FIG. 5) were further studied in human plasma. The reactions were initiated by the addition of 5 μL of a 500 μM DMSO stock solution to 495 μL of preheated plasma solution to yield a final concentration of 5 μM. The assays were performed in a heat block at 37° C. and conducted in duplicate. Samples (50 μL) were taken at 0, 30, 60, 120, 240 min and added to 150 μL acetonitrile in order to deproteinize the plasma. The samples were subjected to vortex mixing for 1 min and then centrifugation for 15 min at 14,000 rpm. The clear supernatants were analyzed by LC-MS.

The in vitro plasma half-life (t½) was calculated using the expression $t½ = \ln(2)/b$ where b is the slope found in the linear fit of the natural logarithm of the fraction remaining of the parent compound vs. incubation time.

The results are shown in Table 2. In the case of plasma stability, SX-682 is roughly as stable as SX-576 in contradistinction to its markedly enhanced stability in liver microsomes. Apparently, eliminating the ring nitrogen has little impact on plasma stability. On the other hand, also changing the sulfur to oxygen in SX-671 resulted in a pronounced 35-fold reduction in plasma half-life. However, keeping the sulfur is insufficient alone to maintain plasma stability as illustrated by SX-517, which maintains the sulfur but eliminates the ring $F_3CO$ group and results in a 5-fold reduction in plasma half-life.

TABLE 2

Stability in human plasma (incubation at 37° C., LC-MS/MS detection)

| Parameter | SX-517 | SX-576 | SX-671 | SX-677 | SX-678 | SX-682 |
|---|---|---|---|---|---|---|
| t½ (min) | 113 | 533 | 21 | 2310 | 3465 | 693 |

Formulation Example 1: Spray Dry Dispersion (SDD) of SX-682 onto Hypromellose Phthalate (HPMCP)

An alternative method to increase oral bioavailability of drug products is through spray dry dispersion in a polymer carrier matrix, which utilizes the spray drying of the active pharmaceutical ingredient (API) and polymer in an organic solvent. Upon drying, the API is amorphously dispersed in the polymer matrix. The polymer matrix is water soluble, and allows for the slow release of API upon exposure to aqueous environments. Spray dry dispersion was performed at Emerson Resources (Norristown, Pa.). SX-682 (250 g) was first dissolved in acetone/water (97:3, 10 liters). HPMCP, 750 g, was then added. The in-process control is to check the clarity of the feed solution and report the result. The material is then spray dried using a GEA Mobile Minor spray dryer using nitrogen as the drying gas. The inlet temperature is set at 90° C., and the outlet temperature is 55-60° C. The nozzle size used was 1 mm. The SX-682 spray solution concentration is 10%, and the atomization nitrogen was set at 1.8 bar, 50%. The formulated powder is collected from both the cyclone and the cartridge filter and post-dried. The powder is bag-blended and double bagged with dessicant pouches for storage. The spray-dried dispersion was suspended in aqueous 0.5% methylcellulose (400 cps) prior to oral dosing in preclinical models.

Pharmacology Example 4: Inhibition of MDSC Migration

A large body of evidence indicates that chronic inflammation as occurs in inflammatory bowel disease is one of several key risk factors for cancer initiation, progression, and metastasis. In an azoxymethane/dextran sulfate sodium (AOM/DSS) model of colitis-associated cancer, Katoh, 2013, *Cancer Cell*, 24:631-44, presented genetic evidence ($Cxcr2^{-/-}$) that loss of CXCR2 dramatically suppressed chronic colonic inflammation and colitis-associated tumorigenesis by inhibiting MDSC recruitment into colonic mucosa and tumors. CXCR2 ligands CXCL1, CXCL2 and CXCL5 were all elevated in inflamed colonic mucosa and tumors and induced MDSC chemotaxis. Adoptive transfer of wild-type MDSCs into $Cxcr2^{-/-}$ mice restored AOM/DSS-induced tumor progression. Deletion of Cxcr2 did not affect infiltration of dendritic cells, T cells, NK or NKT cells. Deletion of Cxcr2 significantly decreased the migratory ability of MDSCs in vitro and in vivo. MDSCs accelerated tumor growth by inhibiting CD8+ T cell cytotoxic activity. Their results showed that CXCR2 was required for homing of MDSCs into colonic mucosa and colitis-associated tumors, revealing a role of CXCR2 in the recruitment of MDSCs from the circulatory system to local tissues and tumors. The results from adoptive transfer of MDSCs provide direct evidence that MDSCs contribute to colonic tumor formation and growth by inhibiting CD8+ T cell cytotoxicity against tumor cells. The authors conclude, "our findings provide a rationale for the development of therapeutic approaches to subvert . . . tumor-induced immunosuppression by using CXCR2 antagonists . . . "

Figure 7:
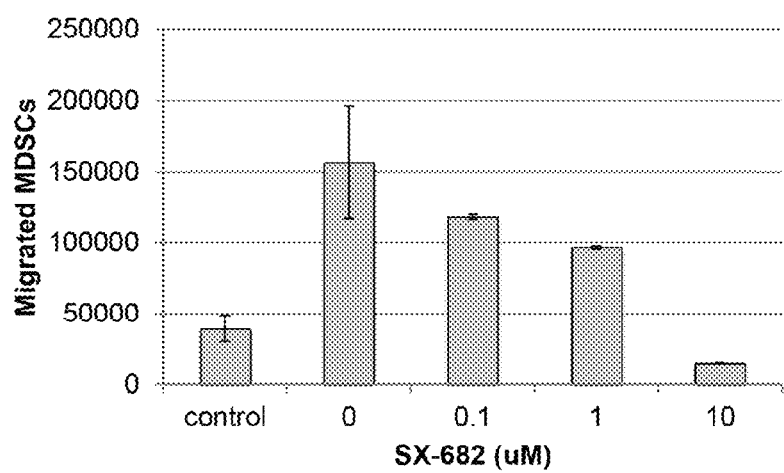
FIG. 7 shows the results of inhibition of myeloid derived suppressor cells (MDSCs) migration by SX-682 in a dose-dependent fashion. The graph shows SX-682 concentration, micromolar (μmolar), vs. the number of migrating MDSCs as measured by flow cytometry. As a control, an aqueous solution with carrier solvent DMSA was used (0 μmolar).
Figure 8A:
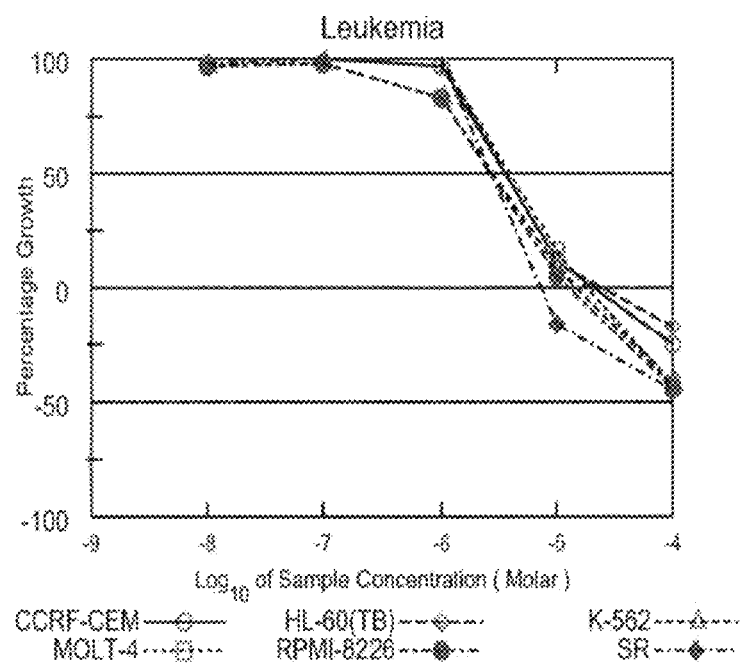
FIG. 8A shows the results of direct inhibition of tumor cell proliferation of leukemia cell lines by SX-682 in a dose-dependent fashion. The leukemia cell lines included CCRF-CEM, MOLT-4, HL-60, RPMI-8226, K-562 and SR. These were independently culture in grown medium at five concentrations of SX-682 between $10^{-8}$ M to $10^{-4}$ molar. Percentage growth inhibition was measured by dye adsorption.
Figure 8B:
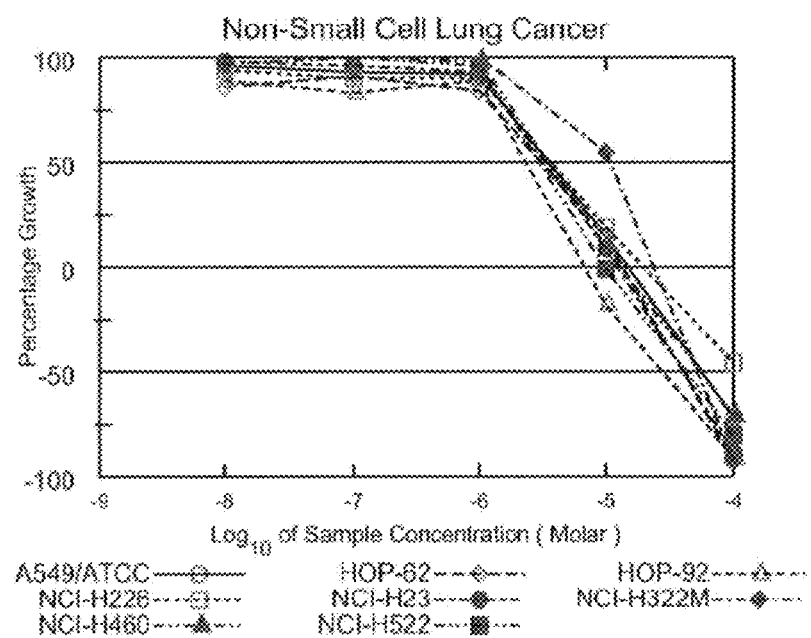
FIG. 8B shows the results of direct inhibition of tumor cell proliferation of non-small cell lung cancer cell lines by SX-682 in a dose-dependent fashion as measured in FIG. 7A. The non-small cell lung cancer cell lines included A549, H226, H460, H23, H522, H322M, HOP-62, and HOP-92.
Figure 8C:
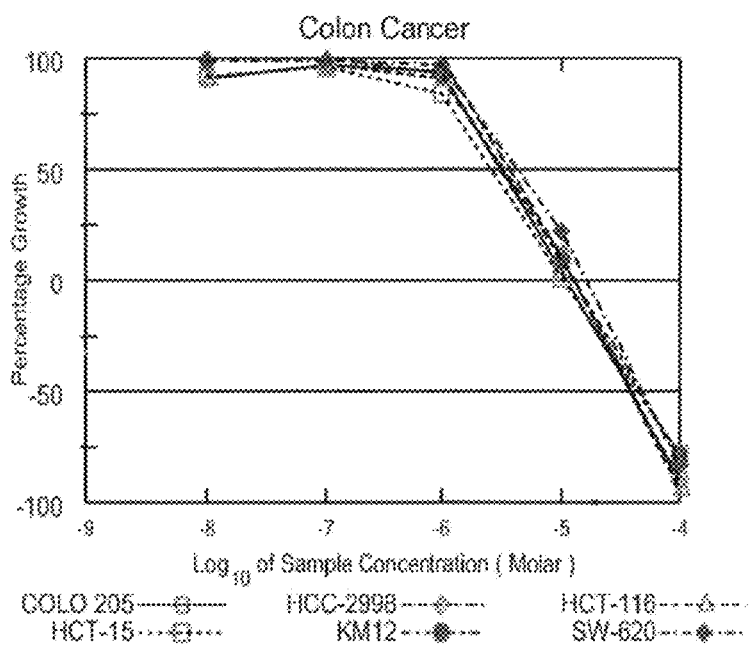
FIG. 8C shows the results of direct inhibition of tumor cell proliferation of colon cancer cell lines by SX-682 in a dose-dependent fashion as measured in FIG. 7A. The colon cancer cell lines included COLO 205, HCT-15, HCC-2998, KM12, HCT-116, and SW-620.
Figure 8D:
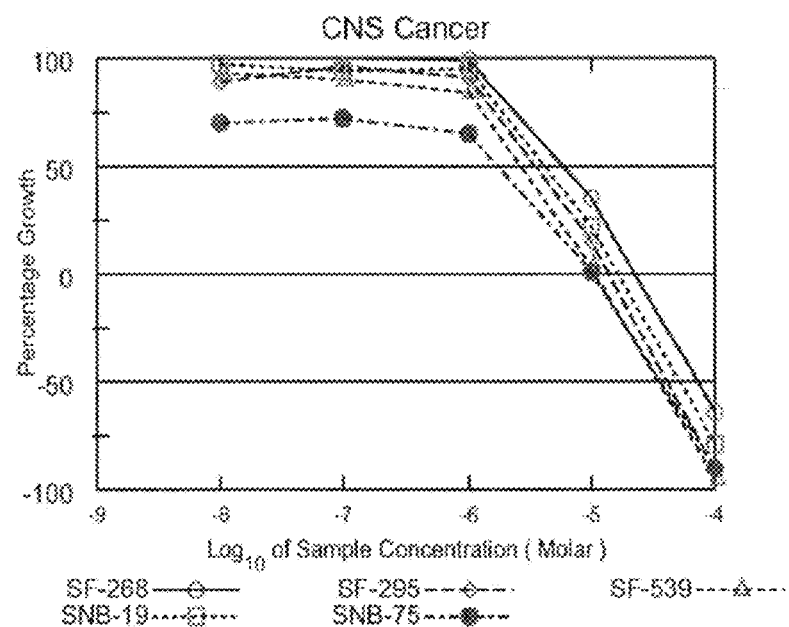
FIG. 8D shows the results of direct inhibition of tumor cell proliferation of CNS cancer cell lines by SX-682 in a dose-dependent fashion as measured in FIG. 7A. The CNS cancer cell lines included SF-268, SNB-19, SF-295, SNB-75, and SF-539.
Figure 8E:
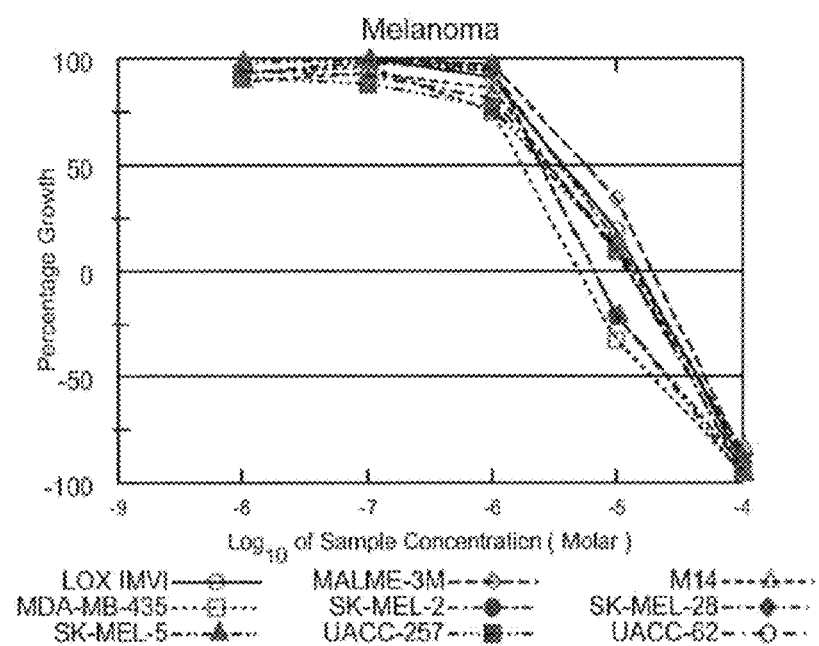
FIG. 8E shows the results of direct inhibition of tumor cell proliferation melanoma cell lines by SX-682 in a dose-dependent fashion. The melanoma cell lines included LOX IMVI, MDA-MB-435, SK-MEL-5, MALME-3M, SK-MEL-2, UACC-257, M14, SK-MEL-28, and UACC-62.
Figure 8F:
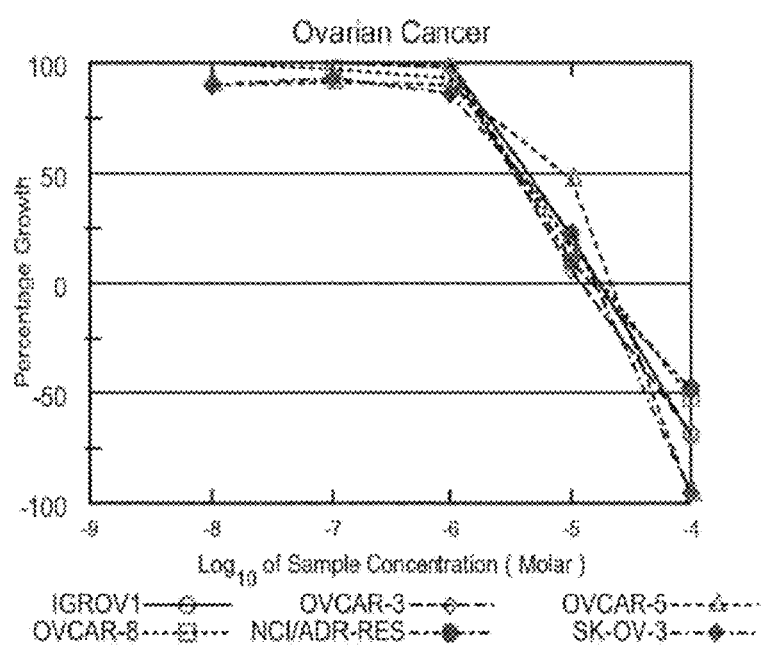
FIG. 8F shows the results of direct inhibition of tumor cell proliferation of ovarian cancer cell lines by SX-682 in a dose-dependent fashion. The ovarian cancer cell lines included IBROV1, OVCAR-8, OVCAR-3, NCI/ADR-RES, OVCAR-5, and SK-OV-3.
Figure 8G:
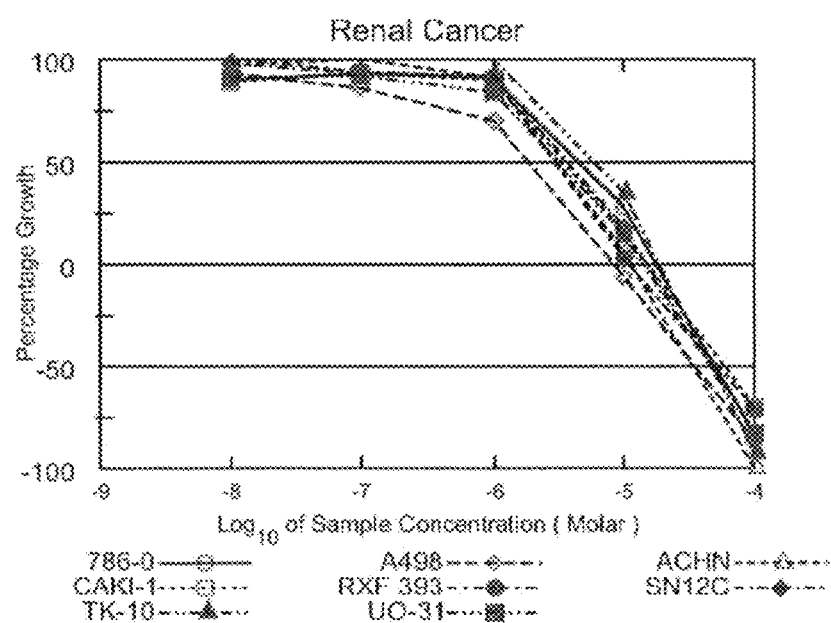
FIG. 8G shows the results of direct inhibition of tumor cell proliferation of renal cancer cell lines by SX-682 in a dose-dependent fashion. The renal cancer cell lines included 786-0, CAK-1, TK-10, RXF 393, UO-31, ACHN, and SN12C.
Figure 8H:
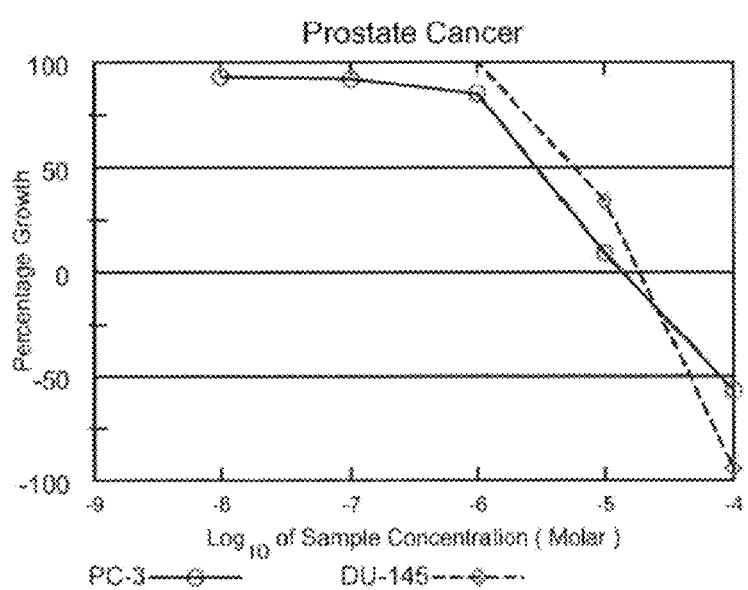
FIG. 8H shows the results of direct inhibition of tumor cell proliferation of prostate cancer cell lines by SX-682 in a dose-dependent fashion. The prostate cancer cell lines included PC-3 and DU-145.
Figure 8I:
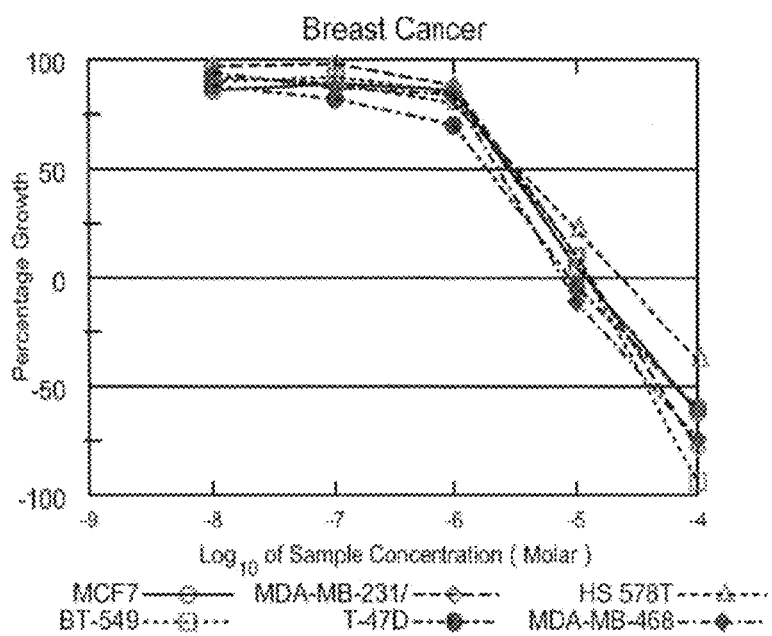
FIG. 8I shows the results of direct inhibition of tumor cell proliferation of breast cancer cell lines by SX-682 in a dose-dependent fashion. The breast cancer cell lines included MCF7, BT-549, MDA-MB-231, T-47D, HS 578T, and MDA-MB-468.

Antagonist SX-682 was used to validate the concept of using a small molecule antagonist of CXCR1 and CXCR2 receptors to block MDSC migration. Using the of method of Katoh, 2013, *Cancer Cell*, 24:631-44 (herein incorporated by reference), to induce and isolate MDSCs, male BALBc mice were given a single intraperitoneal injection of azoxymethane (AOM, 10 mg/kg). Seven days later, these mice were given 4 cycles of water and water containing 1.25% dextran sulfate sodium (DSS). One cycle consisted of providing mice with regular drinking water for 7 days, followed by 1.25% aqueous DSS for 7 days, followed by regular drinking water for 7 days. MDSCs were isolated from femurs and blood of AOM/DSS-treated BALBc mice using the Myeloid-Derived Suppressor Cell Isolation Kit (Miltenyi Biotec) after lysis of red blood cells (RBC) according to the manufacturer's instructions. GROα (CXCL1) was placed in the bottom chamber of a 24-well plate at a concentration of 100 ng/ml. MDSCs isolated from blood of AOM/DSS-treated BALBc mice were seeded at a density of $1 \times 10^6$/well in the upper chamber (3 μm, BD Falcon). After incubation for 12 hours, migrated cells were quantified by flow cytometry using CountBright Absolute Counting Beads (Molecular Probes). To evaluate the effect of SX-682 on GROα-mediated MDSC migration, aqueous DMSO solutions of SX-682 were added to the MDSC-seeded wells prior to migration. The test concentrations of SX-682 were 0.1, 1 and 10 μM, and the DMSO concentration was ≤1%. The results showed that SX-682 was able to effectively inhibit GROα-mediated MDSC migration in a dose-dependent manner (FIG. 7).

Pharmacology Example 5: Inhibition of Tumor Cell Proliferation by SX-682 in a Dose-Dependent Manner The chemokine CXCL8 and its receptors CXCR1 and CXCR2 have been identified as important mediators of cellular proliferation for a number of tumor cell types. To validate the relationship between CXCR1 and CXCR2 receptor antagonism and inhibition of tumor cell proliferation, SX-682 was evaluated against the 60 human tumor cell line panel at five concentration levels (0.01, 0.1, 1, 10, 100 μM) as performed by the Developmental Therapeutics Program at the National Cancer Institute (Shoemaker, 2006, *Nat Rev Cancer*, 6:813-23).

The human tumor cell lines of the cancer screening panel were grown in RPMI 1640 medium containing 5% fetal bovine serum and 2 mM L-glutamine. Cells were inoculated into 96 well microtiter plates in 100 μL at plating densities ranging from 5,000 to 40,000 cells/well depending on the doubling time of individual cell lines. After cell inoculation, the microtiter plates were incubated at 37° C., 5% $CO_2$, 95% air and 100% relative humidity for 24 h prior to addition of SX-682.

After 24 h, two plates of each cell line are fixed in situ with TCA, to represent a measurement of the cell population for each cell line at the time of drug addition (Tz). SX-682 was solubilized in dimethyl sulfoxide at 400-fold the desired final maximum test concentration and stored frozen prior to use. At the time of SX-682 addition, an aliquot of frozen concentrate was thawed and diluted to twice the desired final maximum test concentration with complete medium containing 50 μg/ml gentamicin. Additional four, 10-fold or ½ log serial dilutions are made to provide a total of five drug concentrations plus control. Aliquots of 100 μl of these different drug dilutions were added to the appropriate microtiter wells already containing 100 μl of medium, resulting in the required final drug concentrations.

Following drug addition, the plates were incubated for an additional 48 h at 37° C., 5% $CO_2$, 95% air, and 100% relative humidity. For adherent cells, the assay was terminated by the addition of cold TCA. Cells were fixed in situ by the gentle addition of 50 μl of cold 50% (w/v) TCA (final concentration, 10% TCA) and incubated for 60 minutes at 4° C. The supernatant was discarded, and the plates were washed five times with tap water and air dried. Sulforhodamine B (SRB) solution (100 μl) at 0.4% (w/v) in 1% acetic acid was added to each well, and plates were incubated for 10 minutes at room temperature. After staining, unbound dye was removed by washing five times with 1% acetic acid and the plates were air dried. Bound stain was subsequently solubilized with 10 mM TRIS, and the absorbance was read on an automated plate reader at a wavelength of 515 nm. For suspension cells, the methodology is the same except that the assay was terminated by fixing settled cells at the bottom of the wells by gently adding 50 μl of 80% TCA (final concentration, 16% TCA). Using the seven absorbance measurements (time zero, (Tz), control growth, (C), and test growth in the presence of drug at the five concentration levels (Ti)), the percentage growth was calculated at each of the drug concentrations levels. Percentage growth inhibition was calculated as:

$(Ti-Tz)/(C-Tz) \times 100$ for concentrations for which $Ti >/= Tz$ $(Ti-Tz)/Tz \times 100$ for concentrations for which $Ti < Tz$.

Three dose response parameters were calculated for each experimental agent. Growth inhibition of 50% (GI50) is calculated from $[(Ti-Tz)/(C-Tz)] \times 100 = 50$, which was the drug concentration resulting in a 50% reduction in the net protein increase (as measured by SRB staining) in control cells during the drug incubation. The drug concentration resulting in total growth inhibition (TGI) is calculated from Ti=Tz. The LC50 (concentration of drug resulting in a 50% reduction in the measured protein at the end of the drug treatment as compared to that at the beginning) indicating a net loss of cells following treatment is calculated from $(Ti-Tz)/Tz \times 100 = -50$. Values are calculated for each of these three parameters if the level of activity is reached; however, if the effect is not reached or is exceeded, the value for that parameter is expressed as greater or less than the maximum or minimum concentration tested.

The results (FIGS. 8A, 8B, 8C, 8D, 8E, 8F, 8G, 8H, and 8I) validated the ability of SX-682 to directly affect the proliferation of human tumor cells in the absence of other cells (e.g., MDSCs) through CXCR1/2 antagonism.

Figure 9:
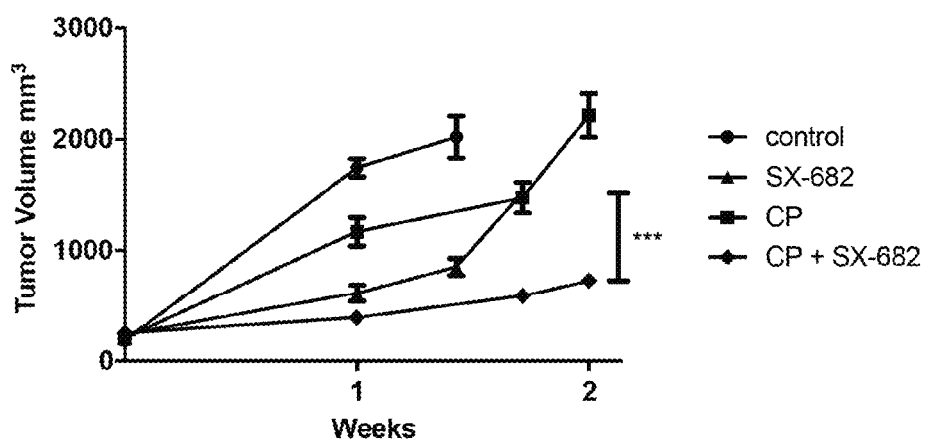
FIG. 9 shows that SX-682 alone or in combination with carboplatin (CP) was an effective therapy for breast cancer in a validated mouse model. The volume ($mm^3$) of tumors in T11 genetically engineered mice was measured during 1-2 week treatment by daily oral administration of SX-682 (10 mg/day/mouse) with or without administration by weekly IP injection of CP (50 mg/kg). The mean, SE, and statistical significance of P<0.0001 (***) for cohorts of seven mice are shown.

Pharmacology Example 6A: Efficacy of CXCR1/2 Antagonism as Single Therapy and in Combination with Carboplatin in the T11 Mouse Model of Breast Cancer The T11 model is a validated mouse model of breast cancer, which derives from the serial orthotopic transplantation of a murine breast tumor derived from a p53-null mouse into a syngeneic p53 competent recipient, and features sporadic, somatic K-Ras mutation (Herschkowitz, 2012, *Proc Natl Acad Sci*, 109:2778-83, herein incorporated by reference). Tumors from the T11 model display an RNA expression pattern characteristic of the human claudin-low disease, and are extremely aggressive, with the majority of untreated animals surviving less than 21 days from the time of enrollment in the therapy studies. Treatment regimens were started following tumor manifestation. SX-682 was given orally via medicated feed, at an approximate dose of 10 mg/day/mouse. In brief, the medicated feed was prepared by Research Diets (New Brunswick, N.J.) by incorporating 15.2 grams of SX-682 spray dried dispersion (as prepared in Formulation Example 1) into 1042 grams of standard rodent diet with 10% kcals from fat. The medicated feed was formed into pellets. Carboplatin (CP) was administered once weekly via intraperitoneal injection at a dose of 50 mg/kg. The results (FIG. 9) showed the addition of SX-682 to carboplatin significantly reduced tumor growth (N=7 each cohort). The combination of SX-682 and CP resulted in a synergistic inhibition of tumor growth and progression in treatment animals, which is a surprising and unexpected result. Mean±SE. ***P<0.0001 (linear regression).

Figure 10:
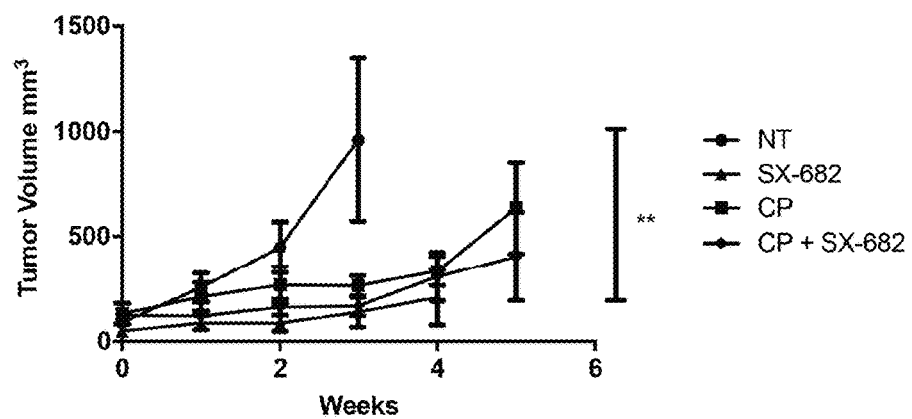
FIG. 10 shows that SX-682 alone or synergistically in combination with CP was an effective treatment for breast cancer in a validated animal model. The volume ($mm^3$) of tumors in C3Tag genetically engineered mice was measured during 4-6 week treatment dosing as in FIG. 9. The mean, SE, and statistical significance of P<0.0001 for cohorts of 10-12 mice are shown.
Figure 11:
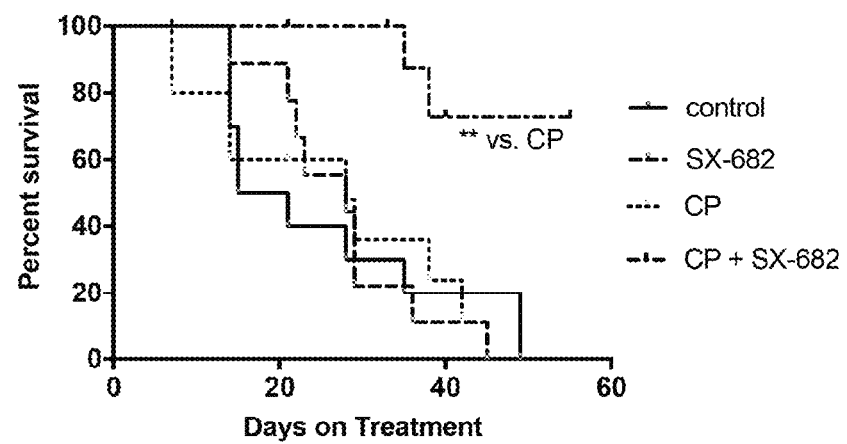
FIG. 11 shows that SX-682 synergized CP to improve survival in a treatment for breast cancer. The treatments were administered in the C3Tag genetically engineered mouse model of breast cancer as described in FIG. 10. The treatment extended for up to 60 days. The results show that the combination therapy (SX-682+CP) significantly improved survival over CP or SX-682 alone (P=0.008).

Pharmacology Example 6B: Efficacy of CXCR1/2 Antagonism as Single Therapy and in Combination with Carboplatin in the C3Tag Mouse Model of Breast Cancer The C31-T-antigen (C3Tag) mouse model is a validated model of human triple-negative basal cell breast cancer as shown by gene expression analysis (Maroulakou, 1994, Proc Natl Acad Sci, 91:11236-40, herein incorporated by reference). The expressed large T-antigen binds and inactivates the RB and p53 tumor suppressor genes, explaining why this model faithfully recapitulates human basal breast cancer, which also harbors RB and p53 inactivation. This model also has frequent K-Ras amplification and infrequent Ras mutations. Treatment regimens were started following tumor manifestation. SX-682 was given orally via medicated feed, at an approximate dose of 10 mg/day/mouse. CP was administered once weekly via intraperitoneal injection at a dose of 50 mg/kg. The results (FIGS. 10 and 11) showed SX-682 treatment alone and in combination with carboplatin significantly reduced tumor growth as compared to untreated controls (N=10-12 per cohort). Mean±SE. **P<0.001 (linear regression). Median survival for vehicle, carboplatin and SX-682 cohorts was 18, 28 and 28 days. Combining SX-682 with CP significantly increased survival compared to carboplatin alone (P=0.008), giving a median survival well beyond 60 days. The combination of SX-682 and CP resulted in a synergistic extension of survival in treatment animals, which is a surprising and unexpected result.

Figure 12:
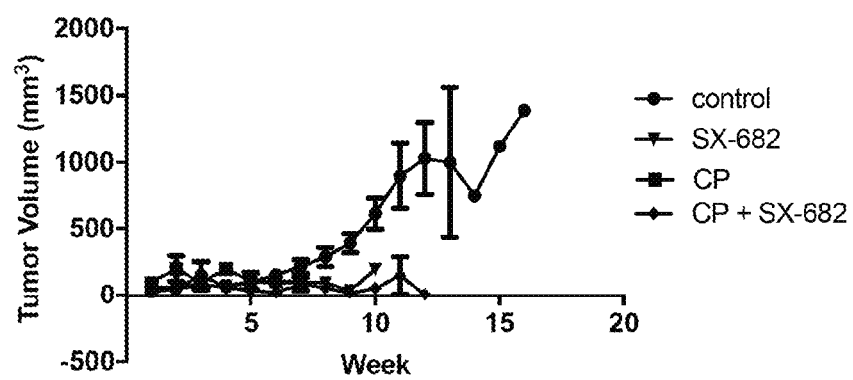
FIG. 12 shows that SX-682 alone or in combination with CP was an effective treatment for melanoma in a validated animal model. The volume (mm$^3$) of tumors in TRIA genetically engineered mice was measured during 15-20 week treatment dosing SX-682 and CP as in FIG. 9. The mean, SE, and statistical significance of P<0.0001 for cohorts of 10-12 mice are shown.
Figure 13:
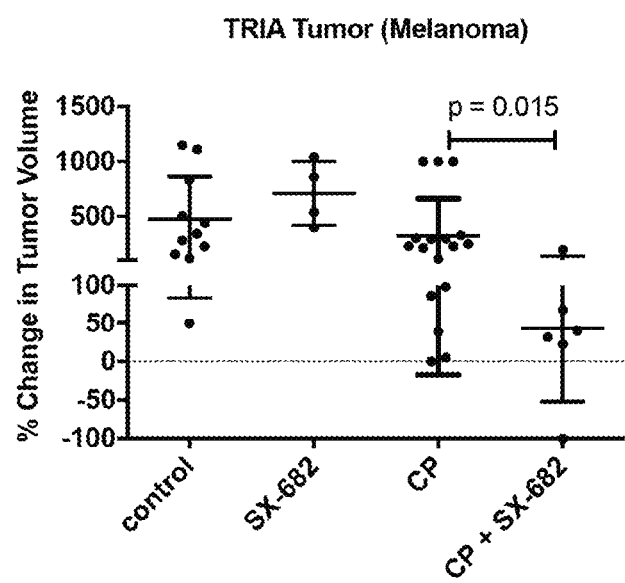
FIG. 13 shows that SX-682 synergized with carboplatin (CP) to cause remission of melanomas in the validated mouse model as described in FIG. 12. 21-days of combination treatment caused a significant percentage change in tumor volume in TRIA genetically engineered mice compared to CP treatment alone.

Pharmacology Example 6C: Efficacy of CXCR1/2 Antagonism as Single Therapy and in Combination with Carboplatin in the TRIA Mouse Model of Melanoma The Tyrosine-Hras/Ink/Arf null (TRIA) is a validated mouse model of melanoma features an immuno-competent autochthonous tumor; Ras events are in >70% of all melanomas, and ~50% lose the INK4a/ARF locus which, with B-RAF mutations, is the most common lesion of this cancer (Sharpless, 2016, Cancer Cell, 29:832-45). Treatment regimens were started following tumor manifestation. SX-682 was given orally via medicated feed, at an approximate dose of 10 mg/day/mouse. CP was administered once weekly via intraperitoneal injection at a dose of 50 mg/kg. The results of this experiment can be seen in FIGS. 12 and 13. SX-682 treatment alone significantly slowed tumor growth comparable to CP alone. SX-682 combination therapy did better than monotherapy and achieved complete remission (zero tumor volume) in 5 of 11 animals. The combination of SX-682 and CP resulted in a synergistic inhibition of tumor growth and progression in treatment animals, which is a surprising and unexpected result.

Pharmacology Example 6D: Efficacy of CXCR1/2 Antagonism as Single Therapy and in Combination with Temozolomide in a Mouse Model of Glioblastoma Multiforme Mouse glioma cell line GL261 is frequently used in experimental models of glioblastoma to evaluate various experimental modalities. Szatmari, 2006, Cancer Sci, 97:546-55 (herein incorporated by reference). To test the hypothesis that dual CXCR1/2 antagonism may potentiate anti-tumor effects of chemotherapy in a mouse model of glioblastoma, tumor-bearing C57BL/6 mice are dosed with CXCR1/2 antagonist alone and in combination with temozolomide (TMZ). Mouse syngeneic tumor GL261 cells are grown with Dulbecco modified Eagle medium supplemented with 10% fetal bovine serum as well as streptomycin (100 mg/mL) and penicillin (100 U/mL) at 37° C. in a humidified atmosphere of 95% air/5% $CO_2$. Mouse glioma GL261 cells are cultured, harvested, and injected into the lower right flank of each C57BL/6 mouse. For the subcutaneous model, $10^6$ GL261 cells are injected into the lower right flank of each C57BL/6 mouse. TMZ is dosed via intraperitoneal injection according to body weight (20 mg/kg). CXCR1/2 antagonist is dosed via oral administration daily. At the beginning of treatment, mice are either randomized by tumor volume or by body weight. The number of animals per group range from between 10-12 animals per group as determined based on Good Statistical Practice analysis. Both tumor and body weight measurements are collected twice weekly and tumor volume is calculated using the equation $(L \times W^2)/2$, where L and W refer to the length and width dimensions, respectively. Error bars are calculated as standard error of the mean. The general health of mice is monitored daily and all experiments are conducted in accordance to AAALAC and institution-based IACUC guidelines for humane treatment and care of laboratory animals. Kaplan-Meier statistical analysis is performed using the Log-rank test using GraphPad Prism.

Figure 14:
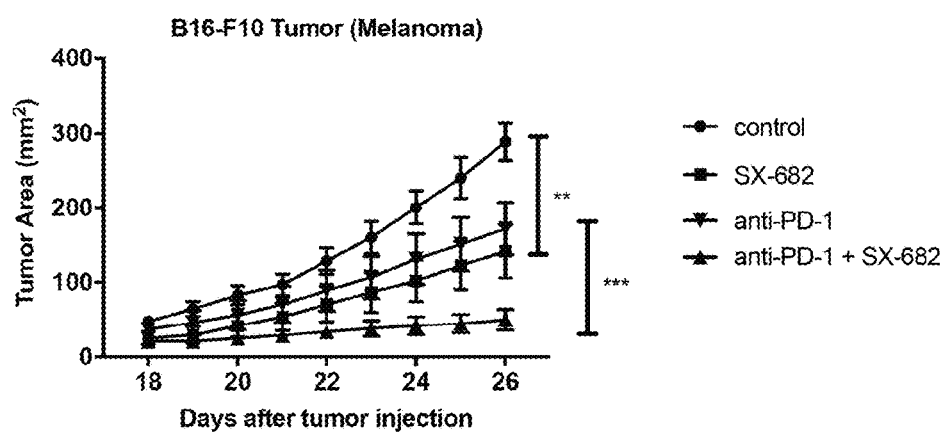
FIG. 14 shows that SX-682 alone or in combination with anti-PD-1 antibody was effective in treating melanomas in a mouse model. The tumor area (mm2) in B16-F10 syngeneic mice was measured during 26 days of treatment with SX-682 orally administered twice daily (50 mg/kg) with and without 100 µg anti-PD-1 administered twice weekly by IP injection. SX-682 monotherapy significantly slowed tumor growth vs. control (P=0.0002, ) and synergized with anti-PD1 therapy vs. monotherapy with either SX-786 or anti-PD-1 (P<0.0005, *). Data and error bars are the mean±SE of 4 or 5 mice per cohort.

Pharmacology Example 7A: Efficacy of CXCR1/2 Antagonism as Single Therapy and in Combination with Anti-PD1 Antibody in the B16-F10 Syngeneic Mouse Model of Melanoma The B16-F10 mouse model is an established model of melanoma, Overwijk, 2001, CURR PROTOC IMMUNOL, Chapter 20: Units 20-21 (herein incorporated by reference), which was used to evaluate the effect of SX-682 alone and in combination with anti-PD1 antibody. B16-F10 mouse melanoma cells were cultured, then mice were injected with 0.5×106 B16-F10 cells on day 0, and treatment was initiated on day 18. Mice were treated with vehicle (control), SX-682 alone (50 mg/kg twice daily, oral), anti-PD-1 alone (100 µg twice weekly, ip), or SX-682 in combination with anti-PD-1 (N=4-5 per cohort). SX-682 was used as a spray dried dispersion (Formulation Example 1), and was administered to mice via oral gavage as a suspension in 0.5% aq methylcellulose. The results (FIG. 14) showed SX-682 monotherapy significantly slowed tumor growth (P=0.0002, linear regression) and potently synergized with anti-PD1 therapy with the combination significantly better than either therapy alone (P<0.0005 for both comparisons). Data and error bars are the mean±SE. The combination of SX-682 and immune checkpoint inhibition resulted in a synergistic inhibition of tumor growth and progression in treatment animals, which is a surprising and unexpected result.

Figure 15:
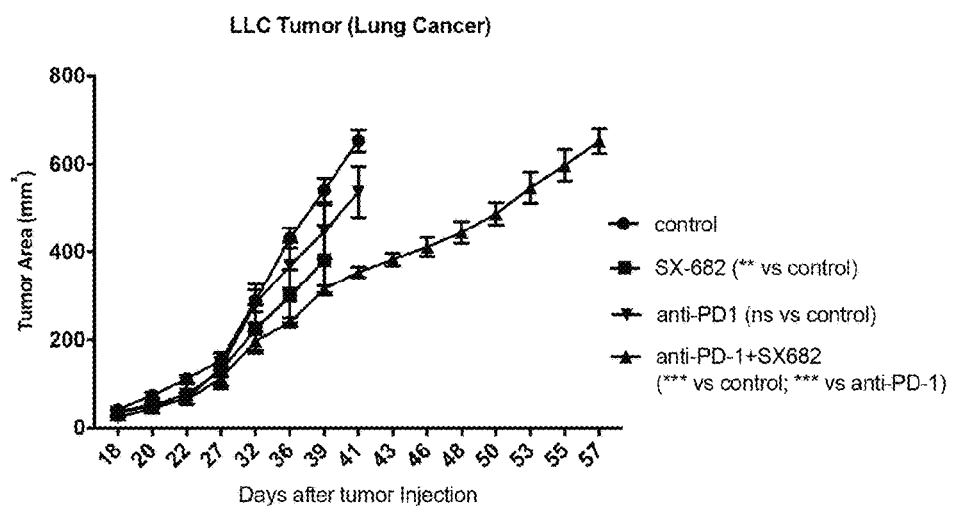
FIG. 15 shows that SX-682 alone or in combination with anti-PD-1 antibody inhibited lung cancer in a validated animal model using the dosing amounts as in FIG. 14. Tumor area (mm2) was measured in LLC syngeneic mice. SX-682 monotherapy significantly slowed tumor growth vs. control (P=0.0002, ) and synergized with anti-PD1 therapy vs. monotherapy with either SX-682 or anti-PD-1 (P<0.002, *). Data and error bars are the mean±SE in cohorts of 5 mice.
Figure 16:
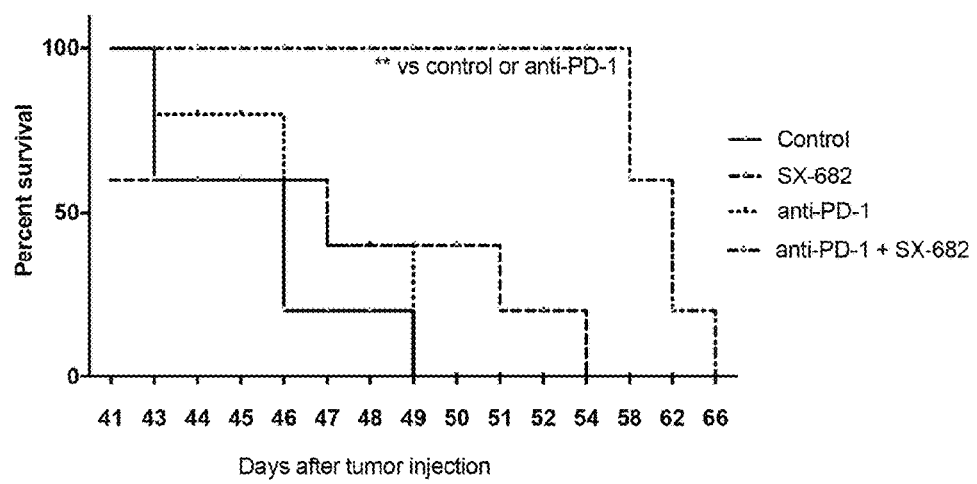
FIG. 16 shows that SX-682 synergized with anti-PD-1 antibody to increase survival in the LLC syngeneic mice as described in FIG. 15. Drug administration and survival determinations continued up to 66 days after tumor injection. The combination of SX-682 and anti-PD-1 therapy significantly enhanced survival compared to vehicle or anti-PD-1 therapy alone (P=0.002).

Pharmacology Example 7B: Efficacy of CXCR1/2 Antagonism as Single Therapy and in Combination with Anti-PD1 Antibody in the LLC Syngeneic Mouse Model of Lung Cancer The Lewis lung carcinoma (LLC) mouse model (Kellar, 2015, Biomed Res Int, 2015:621324, herein incorporated by reference) was used to evaluate the effect of SX-682 alone and in combination with anti-PD-1 antibody. LLC mouse melanoma cells were cultured, then mice were injected with 0.5×106 LLC cells on day 0, and on day 18 treatment was initiated. Mice were treated with vehicle (control), SX-682 alone (50 mg/kg twice daily, oral), anti-PD-1 alone (100 µg twice weekly, ip), or SX-682 in combination with anti-PD-1 (N=5 per cohort). SX-682 was used as a spray dried dispersion (Formulation Example 1), and was administered to mice via oral gavage as a suspension in 0.5% aq. methylcellulose. The results of this experiment can be seen in FIGS. 15 and 16. SX-682 monotherapy significantly slowed tumor growth (P=0.0076, linear regression), and potently synergized with anti-PD1 therapy with the combination significantly better than either therapy alone (P<0.0001 for both comparisons). The combination of SX-682 and anti-PD-1 therapy significantly enhanced survival compared to vehicle or anti-PD-1 therapy alone (P=0.002). The combination of SX-682 and immune checkpoint inhibition resulted in a synergistic effect on both tumor growth and survival in treatment animals, which is a surprising and unexpected result.

Figure 17:
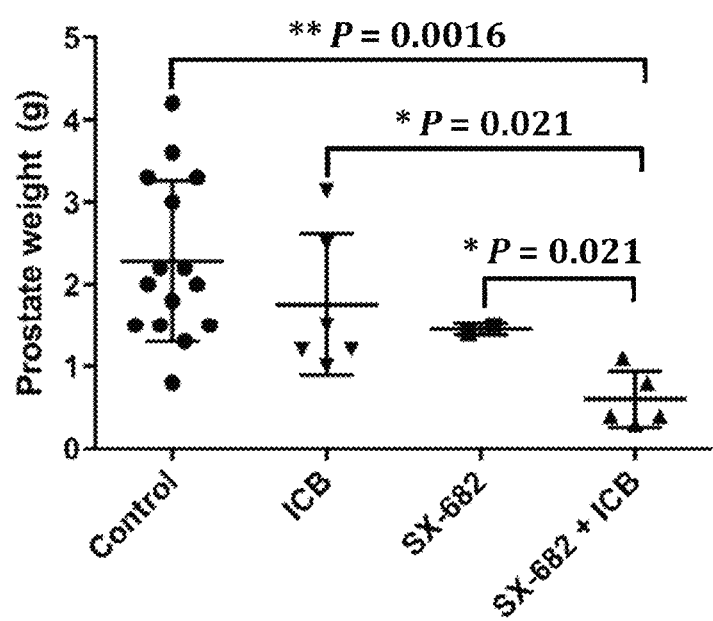
FIG. 17 shows that SX-682 alone and in combination with immune checkpoint blockade (anti-PD1 and anti-CTLA4) inhibited prostate cancer in a validated animal model. Ptenpc−/−p53pc−/−Smad4pc−/− mice were administered 50 mg/kg SX-682 by oral gavage b.i.d. and 200 µg each of anti-PD1 and anti-CTLA4 antibodies (ICB), 3×/week. Prostate weight (g) was measured after 4-6 weeks. SX-682 plus ICB was significantly better than control (P=0.0016, **), and ICB or SX682 alone (P=0.021, *) (unpaired t-test). Mean+SE are shown.

Pharmacology Example 7C: Efficacy of CXCR1/2 Antagonism as Single Therapy and in Combination with Anti-PD1 and Anti-CTLA4 Antibody in a Mouse Model of Castration Resistance Prostate Cancer The genetically engineered Ptenpc−/−p53pc−/−Smad4pc−/− mouse is a prostate-specific PB promoter-driven (PB-Cre4) conditional triple knockout model (i.e., prostate-specific deletion of all three tumor suppressors, Pten, p53 and Smad4 occurs in the 'prostate cancer' or 'pc'). It exhibits an aggressive tumor phenotype, and like the human disease, develops spontaneous bone metastases (Ding, 2012, *Cell,* 148:896-907) Ptenpc−/−p53pc−/−Smad4pc−/− mice at 3-4 months of age with established tumors (>150 mm3, as measured by MRI) were treated with either vehicle (control), SX-682 (50 mg/kg b.i.d.), ICB (200 µg each of anti-PD1 and anti-CTLA4 antibodies, 3×/week), or the SX-682 and ICB combination (SX-682+ICB). SX-682 was used as a spray dried dispersion (Formulation Example 1), and was administered to mice via oral gavage as a suspension in 0.5% aq. methylcellulose. Treatment was continued for 4-6 weeks and prostate weights measured to determine tumor burden. The results (FIG. 17) showed SX-682 plus ICB was significantly better than control or either treatment alone (unpaired t-test). Mean+SE. The combination of SX-682 and immune checkpoint inhibition resulted in a synergistic inhibition of tumor growth and progression in treatment animals, which is a surprising and unexpected result.

Pharmacology Example 8A: Cell-Kill Efficacy of CXCR1/2 Antagonism as Single Therapy and in Combination with T-Cell Therapy In Vitro To validate the use of a small molecule CXCR1/2 antagonist to halt the EMT process in tumor cells thereby decreasing immunoresistance, human tumor cells will be exposed in vitro to various doses of SX-682 in the presence of immune effector cells. These studies will be conducted with and without addition of exogenous recombinant IL-8. Tumor cells will be subsequently evaluated for proliferation/survival, expression of epithelial/mesenchymal markers and stemness markers, expression of immune-relevant molecules, and cytotoxic response to various immune effector cells (human antigen-specific T cell lines generated from the blood of cancer patients or healthy donors by using peptide epitopes from the following antigens: CEA, MUC1, brachyury, or natural killer cells isolated from blood of normal donors and left untreated or activated via IL-2)

Pharmacology Example 8B: Efficacy of CXCR1/2 Antagonism as Single Therapy and in Combination with T-Cell Therapy in a Mouse Model of Pancreatic Cancer Although born with histologically normal pancreata, K-rasLSL.G12D/+; p53R172H/+; PdxCre (KPC) mice developed pancreatic intraepithelial neoplasia (PanIN) lesions on an accelerated schedule, and died of pancreatic ductal adenocarcinoma (PDAC) with a median survival of 5.5 months. Metastases were observed ~80% of the animals, at the same sites seen in human PDAC patients (liver, lung, and peritoneum). Tumors arising in this model were found to have many of the immunohistochemical markers associated with human disease, and bore evidence of widespread genomic alterations, a feature that was previously lacking in most genetically engineered mouse models. The KPC mouse model of PDAC is widely used to evaluate treatment modalities in a preclinical setting (Westphalen, 2012, *Cancer J,* 18:502-10, incorporated herein by reference). To test the hypothesis that dual CXCR1/2 antagonism may potentiate anti-tumor effects of T-cell therapy in a mouse model of PDAC, tumor-bearing KPC mice are dosed with SX-682 alone and in combination with T-cell therapy. T-cells are either selected for or engineered towards high affinity binding to a specific protein of interest located on the tumor cell. In the case of PDAC, these proteins of interest may include (but are not limited to) mesothelin, Wilms' tumor antigen, Mucin 1, or Annexin A2. KPC mice will undergo serial high-resolution ultrasound imaging (Vevo 2100) at 8 weeks of age to monitor autochthonous tumor development. Mice are enrolled based on defined pancreatic mass 3-6 mm. At the start of treatment, select cohorts will receive CXCR1/2 antagonist via oral administration daily. For animals undergoing T-cell therapy, they will receive cyclophosphamide once at enrollment (180 mg/kg) followed 6 hours later by intravenous infusion of 1×107 twice-stimulated engineered T cells followed by 1×107 peptide-pulsed irradiated splenocytes. Recipient mice will also receive IL-2 (2×104 IU, i.p.) every other day for 8 days (in timepoint studies) or for 5 days (in survival studies) to promote donor T cell survival and expansion. For serial T cell infusions, mice will receive the same treatment protocol, excluding the cyclophosphamide after the first dose, every 2 weeks. Power analyses will guide enrollment numbers to power the study for a large effect (>50% increase in median overall survival). Both tumor and body weight measurements are collected twice weekly and tumor volume is measured via serial high resolution ultrasound imaging. Error bars are calculated as standard error of the mean. The general health of mice is monitored daily and all experiments are conducted in accordance to AAALAC and institution-based IACUC guidelines for humane treatment and care of laboratory animals. Kaplan-Meier statistical analysis is performed using the Log-rank test using GraphPad Prism.

Pharmacology Example 9: Efficacy of CXCR1/2 Antagonism as Single Therapy and in Combination with Cancer Vaccine in a Mouse Model of Cancer All animal studies re carried out in accordance with the guidelines of the Association for Assessment and Accreditation of Laboratory Animal Care. Experimental studies were carried out under approval of the NIH Intramural Animal Care and Use Committee. Murine colon carcinoma MC38 cells are stably transfected with chorioembryonic antigen (CEA), and subcutaneously implanted into female C57BL/6 mice on day 0. Beginning on day 7, animals are dosed daily with SX-682 via medicated feed. Beginning on day 14, test animals are vaccinated weekly with either Hank's Balanced Salt Solution or 50 mg of a gp70 peptide (p15e) emulsified in Montanide ISA-51-VG (Seppic) at a 1:1 ratio. Evaluation of the effect of SX-682 on various immune cell subsets in non-tumor bearing mice will be evaluated. Spleens will be collected and analyzed for antigen-specific immune responses and various immune cell subsets. Anti-tumor effect of combinations of SX-682 with cancer vaccines will be evaluated. Evaluations will include effect on tumor volume, tumor microenvironment, including tumor phenotype, etc., will be evaluated. Vaccine-specific immune responses will also be measured.

We claim:

1. A method for treating a patient with a cancer, comprising administering to the patient in need thereof a pharmaceutical composition comprising a therapeutically effective amount of a compound having a structure selected from the group consisting of formulas SX-517, SX-576, and SX-682,

SX-517

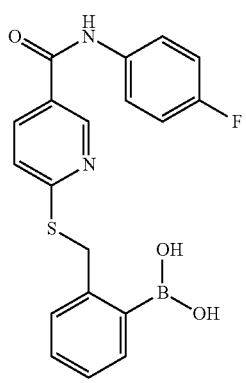

SX-576

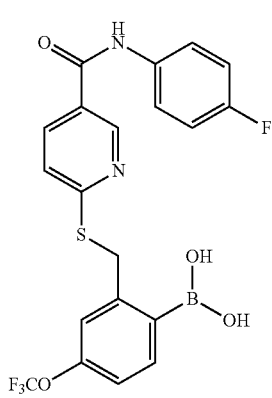

SX-682

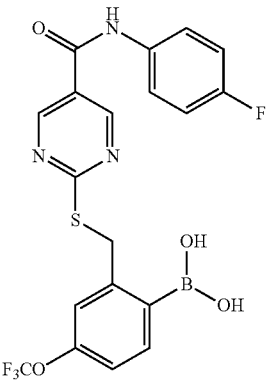

or a pharmaceutically acceptable salt or solvate thereof, and performing at least one of (a), (b), (c) and (d), wherein (a) comprises assaying serum levels of CXCR1 and/or CXCR2 ligands in the patient prior to the treatment, (b) comprises assaying serum levels of CXCR1 and/or CXCR2 ligands in the patient after the treatment, (c) comprises assaying serum levels of myeloid derived suppressor cells (MDSCs) and/or neutrophils in the patient prior to the treatment, and (d) comprises assaying serum levels of MDSCs or neutrophils in the patient after the treatment.

2. The method of claim 1, further comprising administering an anticancer therapy.

3. The method of claim 2, wherein the anticancer therapy is a chemotherapy.

4. The method of claim 3, wherein carboplatin is administered to the patient.

5. The method of claim 2 wherein said anticancer therapy is radiation therapy.

6. The method of claim 1 wherein the compound has the structure of formula SX-682 and the cancer is selected from cancers of the prostate, colorectum, pancreas, cervix, stomach, endometrium, brain, liver, bladder, ovary, testis, head, neck, skin, mesothelial lining, blood, esophagus, breast, muscle, connective tissue, lung, adrenal gland, thyroid, kidney, lymphoid system, bone marrow or bone, glioblastoma, mesothelioma, renal cell carcinoma, gastric carcinoma, sarcoma, choriocarcinoma, cutaneous basocellular carcinoma, and testicular seminoma.

7. The method of claim 1 wherein the compound has the structure of formula SX-682 and the cancer is selected from cancers of the prostate, pancreas, stomach, brain, liver, head, neck, skin, blood, breast, lung, glioblastoma, and mesothelioma.

8. The method of claim 1 wherein the compound has the structure of formula SX-682 and the cancer is breast cancer.

9. The method of claim 8, wherein the pharmaceutical composition is administered orally.

10. The method of claim 9, further comprising administering a platinum chemotherapy.

11. The method of claim 1 wherein the compound has the structure of formula SX-682 and the cancer is a melanoma.

12. The method of claim 11, wherein the pharmaceutical composition is administered orally.

13. The method of claim 12, further comprising administering a platinum chemotherapy.

14. The method of claim 1, wherein the cancer is a lung cancer.

15. The method of claim 14, wherein the pharmaceutical composition is administered orally.

16. The method of claim 1 wherein the compound has the structure of formula SX-682 and the cancer is a prostate cancer.

17. The method of claim 16, wherein the pharmaceutical composition is administered orally.

18. The method of claim 1, wherein the cancer is a glioblastoma.

19. The method of claim 18, wherein the pharmaceutical composition is administered orally.

20. The method of claim 19, further comprising administering temozolomide.

21. The method of claim 1, wherein the cancer is a pancreatic cancer.

22. The method of claim 21, wherein the pharmaceutical composition is administered orally.

* * * * *